(12) United States Patent
Warren

(10) Patent No.: US 10,817,171 B2
(45) Date of Patent: Oct. 27, 2020

(54) IDENTIFICATION SYSTEM INCLUDING A MOBILE COMPUTING DEVICE

(71) Applicant: Apollo 13 Designs, LLC, Lancaster, PA (US)

(72) Inventor: Michael K. Warren, Lancaster, PA (US)

(73) Assignee: Apollo 13 Designs, LLC, Lancaster, PA (US)

( * ) Notice: Subject to any disclaimer, the term of this patent is extended or adjusted under 35 U.S.C. 154(b) by 0 days.

(21) Appl. No.: 16/561,727

(22) Filed: Sep. 5, 2019

(65) Prior Publication Data
US 2020/0004415 A1 Jan. 2, 2020

Related U.S. Application Data

(63) Continuation-in-part of application No. 15/945,943, filed on Apr. 5, 2018, now Pat. No. 10,416,881, and
(Continued)

(51) Int. Cl.
| | |
|---|---|
| G06F 3/0488 | (2013.01) |
| H04W 4/80 | (2018.01) |
| G06F 3/044 | (2006.01) |
| G06F 3/0346 | (2013.01) |
| G06F 3/16 | (2006.01) |
| G06K 7/10 | (2006.01) |
| G06Q 20/32 | (2012.01) |
| G05B 19/048 | (2006.01) |
| A61B 5/00 | (2006.01) |
| A61B 5/0205 | (2006.01) |
| A44C 17/02 | (2006.01) |

(Continued)

(52) U.S. Cl.
CPC ...... *G06F 3/04883* (2013.01); *A44C 17/0233* (2013.01); *A61B 5/02055* (2013.01); *A61B 5/6817* (2013.01); *G05B 19/048* (2013.01); *G06F 3/0346* (2013.01); *G06F 3/044* (2013.01); *G06F 3/162* (2013.01); *G06K 7/10297* (2013.01); *G06Q 20/322* (2013.01); *H04W 4/80* (2018.02); *A44C 9/00* (2013.01); *A61B 5/02438* (2013.01); *G05B 2219/35444* (2013.01); *G06F 2203/0384* (2013.01); *H04L 41/026* (2013.01); *H04W 4/14* (2013.01); *H04W 68/005* (2013.01)

(58) Field of Classification Search
None
See application file for complete search history.

(56) References Cited

U.S. PATENT DOCUMENTS

| | | |
|---|---|---|
| 6,715,911 B2 | 4/2004 | Villarreal |
| 7,040,778 B2 | 5/2006 | Villarreal |
| (Continued) | | |

OTHER PUBLICATIONS

Webpage for www.Ringly.com, downloaded on Dec. 6, 2016, Copyright 2016 Ringly, 4 pages.

*Primary Examiner* — Adolf Dsouza
(74) *Attorney, Agent, or Firm* — Barley Snyder

(57) ABSTRACT

An identification system includes a mobile computing device having a memory and an establishing module establishing an identifying data set stored in the memory. The identifying data set includes an accumulated data gathered at the mobile computing device over an establishing period and is capable of uniquely identifying a user corresponding to the mobile computing device.

15 Claims, 26 Drawing Sheets

Related U.S. Application Data a continuation of application No. 15/262,758, filed on Sep. 12, 2016, now Pat. No. 9,946,457, and a continuation-in-part of application No. 14/179,097, filed on Feb. 12, 2014, now abandoned, and a continuation-in-part of application No. 13/827,341, filed on Mar. 14, 2013, now abandoned.

(60) Provisional application No. 61/713,200, filed on Oct. 12, 2012.

(51) Int. Cl.
| | | |
|---|---|---|
| *H04W 4/14* | (2009.01) | |
| *A44C 9/00* | (2006.01) | |
| *A61B 5/024* | (2006.01) | |
| *H04W 68/00* | (2009.01) | |
| *H04L 12/24* | (2006.01) | |

(56) References Cited

U.S. PATENT DOCUMENTS

| | | | |
|---|---|---|---|
| 7,513,019 | B2 | 4/2009 | Friedman |
| 8,250,796 | B2 | 8/2012 | Padgett |
| 9,565,558 | B2* | 2/2017 | Radpour ............... H04L 9/083 |
| 9,946,457 | B2 | 4/2018 | Warren |
| 2006/0094938 | A1* | 5/2006 | Shimada ................ A61B 5/00 |
| | | | 600/301 |
| 2008/0074329 | A1 | 3/2008 | Caballero et al. |
| 2011/0265314 | A1 | 11/2011 | Brommer et al. |
| 2012/0249797 | A1 | 10/2012 | Haddick et al. |
| 2013/0191741 | A1* | 7/2013 | Dickinson ............. G06F 1/163 |
| | | | 715/702 |
| 2013/0268758 | A1* | 10/2013 | Schrecker ........... H04L 9/3263 |
| | | | 713/168 |
| 2013/0327088 | A1 | 12/2013 | Smith |
| 2014/0027521 | A1 | 1/2014 | Pedicano |
| 2015/0178532 | A1 | 6/2015 | Brule |
| 2017/0189641 | A1* | 7/2017 | Moturu ............... A61B 5/0022 |
| 2018/0225039 | A1 | 8/2018 | Warren |

* cited by examiner

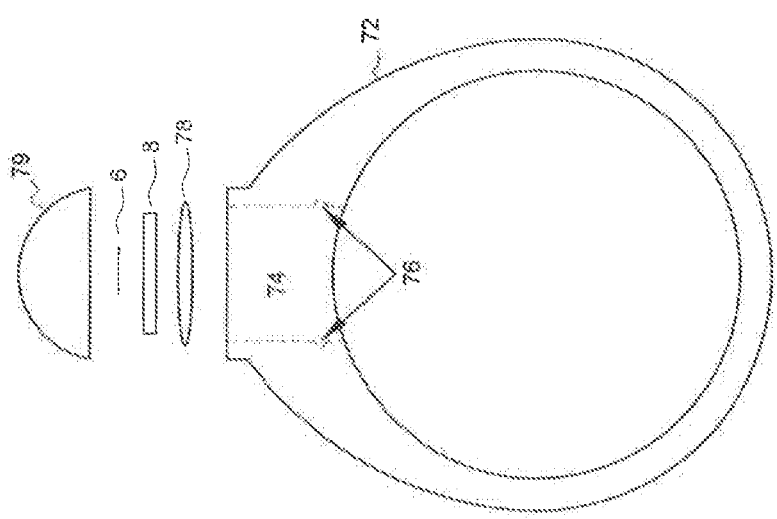

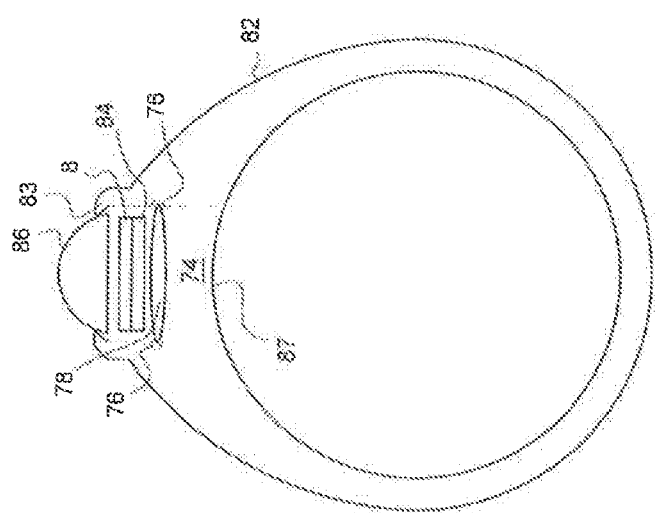

| GESTURES | ACTION | STATE |
|---|---|---|
| GESTURE 1 | VOLUME UP | PLAYING MUSIC |
| GESTURE 2 | VOLUME DOWN | " |
| GESTURE 1 | INITIATE PAIRING | PAIRING |
| GESTURE 2 | END PAIRING | " |
| GESTURE 3 | CONFIRMATION ON PAIRED DEVICE | " |
| ⋮ | ⋮ | ⋮ |

IDENTIFICATION SYSTEM INCLUDING A MOBILE COMPUTING DEVICE

CROSS-REFERENCE TO RELATED APPLICATIONS

This application is a continuation-in-part of U.S. patent application Ser. No. 15/945,943, filed on Apr. 5, 2018, which is a continuation of U.S. patent application Ser. No. 15/262,758, filed on Sep. 12, 2016, which is a continuation-in-part of U.S. patent application Ser. No. 14/179,097, filed on Feb. 12, 2014, which is a continuation-in-part of U.S. patent application Ser. No. 13/827,341, filed on Mar. 14, 2013, which claims the benefit of U.S. Provisional Patent Application No. 61/713,200, filed on Oct. 12, 2012.

FIELD OF THE INVENTION

The present invention relates to a wearable electronic device, and more particularly, to a wearable electronic device having an interface for electronic communications.

BACKGROUND

Mobile computing devices, such as mobile phones, are increasingly prevalent. As additional functions are developed for mobile computing devices, users spend more time using the devices. Known mobile computing devices, however, require a user to look at and interact with a screen in order to use the mobile computing device. Although mobile computing devices are useful in a wide range of applications, the increasing amount of time spent looking at the screen of mobile computing devices detracts from social encounters and also diminishes other interactions of the user with his environment. Mobile computing device users have a need to easily and intuitively utilize the benefits of the mobile computing device without spending large quantities of time looking at the screen.

SUMMARY

An identification system includes a mobile computing device having a memory and an establishing module establishing an identifying data set stored in the memory. The identifying data set includes an accumulated data gathered at the mobile computing device over an establishing period and is capable of uniquely identifying a user corresponding to the mobile computing device.

BRIEF DESCRIPTION OF THE DRAWINGS

The invention will now be described by way of example with reference to the accompanying figures, of which:

FIG. 7 is a schematic cross-section view of an example of a jewelry piece with an interchangeable radio frequency identification tag in accordance with some embodiments of the present disclosure;

FIGS. 8A and 8B are schematic cross-sectional views of an example of a jewelry piece with an interchangeable radio frequency identification tag in accordance with some embodiments of the invention;

DETAILED DESCRIPTION OF THE EMBODIMENT(S)

Figure 1:
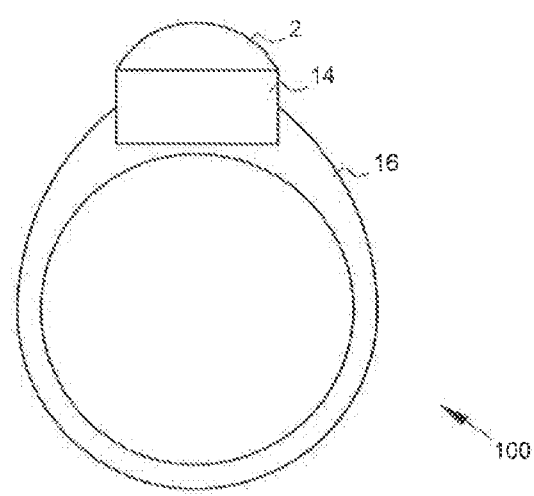
FIG. 1 is a side view of a jewelry piece with an interchangeable radio frequency identification tag in accordance with some embodiments of the present disclosure.

This description of the exemplary embodiments is intended to be read in connection with the accompanying drawings, which are to be considered part of the entire written description. In the description, relative terms such as "lower," "upper," "horizontal," "vertical,", "above,"

"below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

In FIGS. 1 through 6, like items are indicated by like reference numerals and, for brevity, descriptions of a component or structure are not repeated. Materials describing the manufacture of a component in one description can be used to manufacture that component in each embodiment unless specifically stated otherwise.

The present disclosure provides an apparatus comprising a piece of jewelry connected with an interchangeable radio frequency identification (RFID) tag. The apparatus is provided to enable a user to conveniently and unobtrusively carry a RFID tag with a low probability of loss or damage to the tag.

In some embodiments, the jewelry piece is a ring. However, other jewelry pieces would be suitable for use in accordance with the present disclosure. Specifically, the present disclosure could be used to connect an interchangeable RFID tag with watches, pendants, brooches, earrings and other body piercing jewelry, necklaces, bracelets, amulets, medallions, hairpins, and any suitable jewelry pieces.

There are generally three types of RFID tags: active, passive, and battery-assisted passive. In some embodiments of the present disclosure uses a passive tag, which is generally cheaper and smaller than active or battery-assisted passive tags because it requires no independent power source. A passive tag uses the radio energy transmitted by a RFID reader as its power source. However, any type of RFID tag would be suitable for use with the present disclosure. Use of an active or battery-assisted passive RFID tag requires the addition of an independent power source such as a battery to the disclosed apparatus. The active RFID tags embodied in this disclosure are additionally capable of low- or reduced-power modes. In this disclosure, an RFID tag is not necessarily limited to any specific operating frequency. An RFID tag useable with the present invention may also operate with either regulated or unregulated frequencies.

FIG. 1 is a side view of one example of a jewelry piece 100 with an interchangeable RFID tag in accordance with some embodiments of the present disclosure. FIG. 1 shows the exterior of the apparatus with all component pieces assembled. Viewing the exterior, a user or viewer of the apparatus sees a cap 2, a housing 14, and a ring 16, which are described in further detail below.

Figure 2:
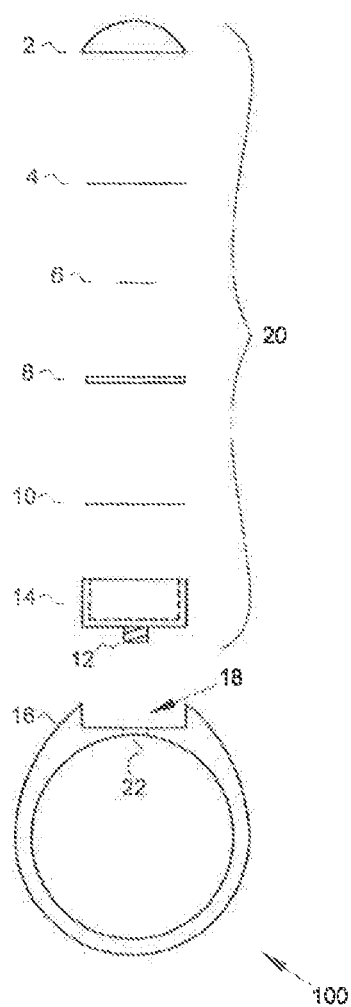
FIG. 2 is a schematic exploded side view of a jewelry piece with an interchangeable radio frequency identification tag in accordance with some embodiments of the present disclosure.

FIG. 2 is a schematic exploded side view of an example of a jewelry piece 100 with an interchangeable RFID tag in accordance with some embodiments of the present disclosure. FIG. 2 illustrates how constituent pieces of the apparatus are fitted together in the illustrated embodiment.

Cap 2 is formed from a gemstone, a synthetic or imitation gemstone, or like material including glass or plastic. Cap 2 is often formed as a "cabochon" having a convex, substantially hemispherical surface and a flat surface. In the alternative, the cap can have a concave surface and a flat surface. The shape of cap 2 can vary, employing any suitable gemstone cutting techniques. Cap 2 is connected to housing 14 by cement, glue, solder, or other suitable adhesive.

Below cap 2 is a RFID tag 6 which may be of any suitable type and configuration but is illustrated as a RFID wafer. RFID tag 6 is disposed within a buffer ring 8. In some embodiments, buffer ring 8 is composed of a ferrite material. Buffer ring 8 is disposed within housing 14. RFID tag 6, buffer ring 8, and the inner diameter of housing 14 are sized to minimize movement of the RFID tag 6 during use of the apparatus.

In some embodiments, the jewelry piece 100 includes one or both of a top spacer 4 and bottom spacer 10 to further minimize movement of RFID tag 6 during use. In some embodiments, top spacer 4 and bottom spacer 10 are composed of a material that does not substantially inhibit radio frequency transmission such as plastic or glass. A material does not substantially inhibit radio frequency transmission if the transmission range is not notably reduced by using that material. Materials that do no substantially inhibit radio frequency transmission, such as glass and plastic, are substantially permissive materials.

In some embodiments, top spacer 4 and bottom spacer 10 are composed of materials which inhibit radio frequency transmission, such as most metal alloys, as a way to limit the range of enclosed RFID tag 6. For example, if RFID tag 6 is readable from a distance of three feet from a jewelry piece 100 without top spacer 4 or bottom spacer 10, but if it is desired that RFID tag 6 only be readable at a distance of six inches from jewelry piece 100, then one or both of top spacer 4 and bottom spacer 10 may comprise a material which inhibits radio frequency transmission, which may be added to jewelry piece 100 to reduce the effective reading range of RFID tag 6. In some embodiments, the range of RFID tag 6 may be limited by the structure of RFID tag 6 or may be limited by programming. Also, spacers may not be necessary to limit the range but may be desired nonetheless to immobilize the contents of jewelry piece 100.

The unit formed by cap 2, RFID tag 6, buffer ring 8, and housing 14, when connected, is referred to as a command module 20. In some embodiments of the present disclosure, command module 20 is fully interchangeable, meaning a first command module connected to ring 16 can be removed and replaced with a second command module.

Housing 14 is formed from stainless steel, precious metal (gold, silver, platinum, and the like), or any suitable material for forming jewelry, such as carbon fiber or titanium alloys. Housing 14 is sized to fit within a receiving area 18 of ring 16. Housing 14 is connected to ring 16 by a screw post 12, which is a threaded member that is rotatably inserted into a threaded slot 22 in ring 16.

Ring 16 is formed from stainless steel, precious metal (gold, silver, platinum, and the like), or any suitable material for forming jewelry, such as carbon fiber or titanium alloys. In some embodiments, ring 16 may be formed from various insulating materials such as ceramic, nylon, acrylic, Lexan, Lucite, or the like, which provide non-radio wave interference properties, allow for low cost of production, low weight, improve esthetics, and can be easy to remove in an emergency.

In some embodiments, a ring formed from ceramic or similar material is given the appearance of a precious metal or other metal through chemical vapor deposition of a metal coating on the exterior surface of the ring. In other embodiments, a ring formed from ceramic or similar material is given the appearance of a precious metal or other metal through ionic beam subsurface deposition of metal below the exterior surface of the ring. Such embodiments have the advantage of appearing as metal rings while having minimal RF interference due to their ceramic construction.

Ring 16 includes a receiving area 18 and threaded slot 22 for receiving housing 14 and screw post 12, respectively. Housing 14 and ring 16 can be formed from the same material or different materials.

Figure 3:
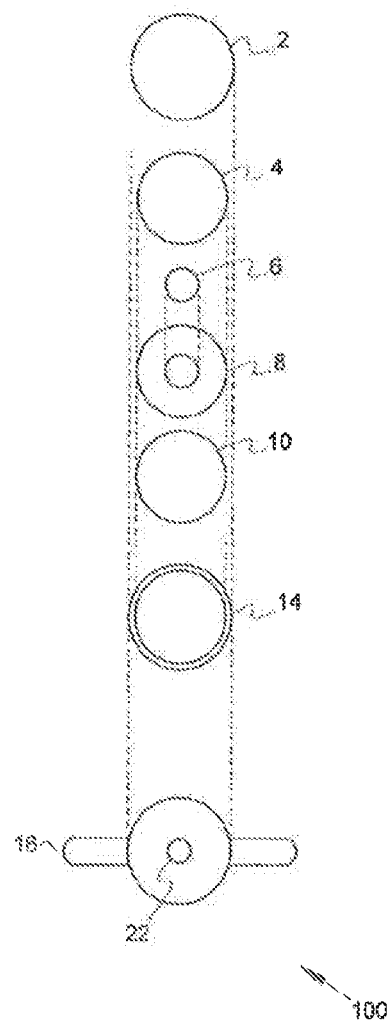
FIG. 3 is a schematic top view, with components again exploded as in FIG. 2, of a jewelry piece with an interchangeable radio frequency identification tag in accordance with some embodiments of the present disclosure.

FIG. 3 is a schematic top view, with components again exploded as in FIG. 2, of a jewelry piece with an interchangeable radio frequency identification tag in accordance with some embodiments of the present disclosure. As in FIG. 2, FIG. 3 illustrates how the constituent components of jewelry piece 100 are fitted together. In the illustrated embodiment, RFID tag 6 is disposed within buffer ring 8, which in turn is disposed within housing 14 along with top spacer 4 and bottom spacer 10. Cap 2 is adhered to housing 14 to form command module 20. Command module 20 is operatively connected to ring 16 via a screw post 12 (not visible in FIG. 3) rotatably inserted into threaded slot 22.

Figure 4:
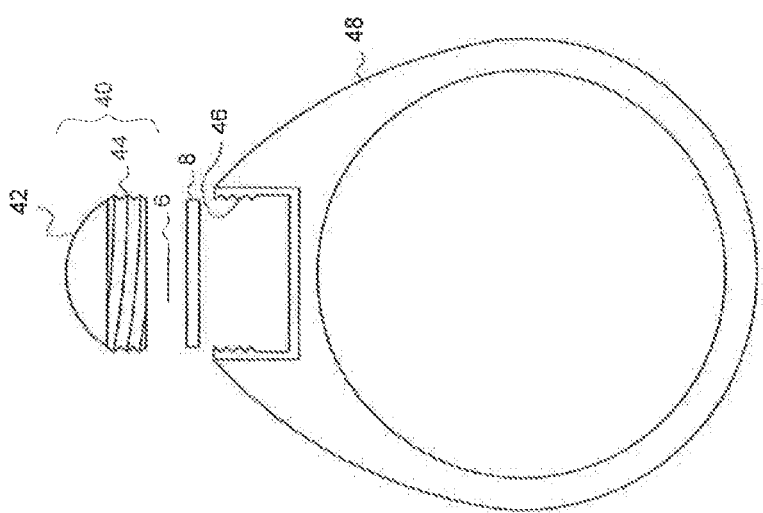
FIG. 4 is a schematic cross-section view of an example of the command module in accordance with some embodiments of the present disclosure.

Referring now to FIG. 4, in some embodiments, cap 40 comprises a top 42 connected to a threaded member 44 which can be rotatably inserted into a threaded recess 46 on ring 48. Top 42 is formed from a gemstone, a synthetic or imitation gemstone, or like material including glass or plastic. Top 42 is adhered or mounted to threaded member 44. A RFID tag 6 is disposed within a buffer ring 8, which is then disposed within threaded recess 46. Cap 40 seals RFID tag 6 and buffer ring 8 within the threaded recess 46 when rotatably inserted into the threaded recess 46. In some embodiments, one or more spacers can be included on either side of RFID tag 6 disposed within buffer ring 8. The one or more spacers can be either substantially permissive or substantially inhibiting, as described above.

In the embodiment shown in FIG. 4, ease of access to an enclosed RFID tag provides another means of interchangeability. In some embodiments, rather than changing out the entire command module 20, a user can unscrew cap 40 from ring 48 to remove cap 40, permitting access to and exchange of the enclosed RFID tag 6.

Figure 5:
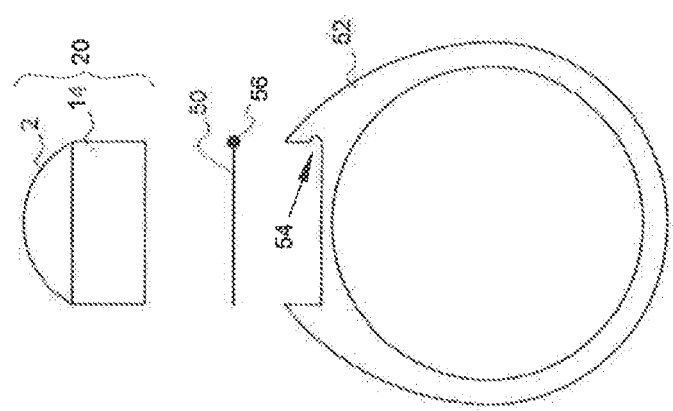
FIG. 5 is a schematic cross-section view of an example of a jewelry piece with an interchangeable radio frequency identification tag in accordance with some embodiments of the present disclosure.

In some embodiments, shown in FIG. 5, the command module 20 is affixed to a modified ring 52 via a retaining clip 50. Retaining clip 50 is shaped to fit about the bottom of housing 14, and has a bulbous protrusion 56 on one side. Retaining clip 50 can also be a standard "C" clip. Once retaining clip 50 is connected to housing 14 using adhesive or simple friction, the entire command module 20 is slid into position, mounted on modified ring 52. The bulbous protrusion 56 is fitted into a groove 54 on modified ring 54, and command module 20 snaps into place on modified ring 52 where it is held by the union of bulbous protrusion 56 and groove 54. In some embodiments, one or more spacers can be disposed within command module 20, on either side of RFID tag 6 disposed within buffer ring 8. The one or more spacers can be either substantially permissive or substantially inhibiting, as described above.

Figure 6:
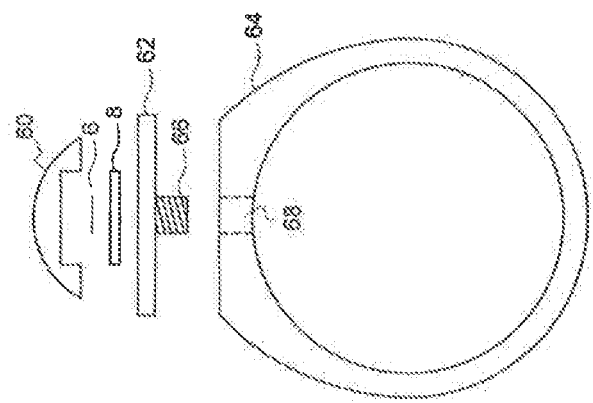
FIG. 6 is a schematic cross-section view of an example of a jewelry piece with an interchangeable radio frequency identification tag in accordance with some embodiments of the present disclosure.

In some embodiments, shown in FIG. 6, a hollow cap 60 is used to hold the RFID tag instead of the previously-described housing. As with previously-described cap 2, hollow cap 60 is formed from a gemstone, a synthetic or imitation gemstone, or like material including glass or plastic. Also, hollow cap 60 has a convex, substantially hemispherical surface and a flat surface. In the alternative, the cap can have a concave surface and a flat surface. Hollow cap 60 has a recess formed in the flat surface to hold an RFID tag 6 and buffer ring 8. In the illustrated embodiment, RFID tag 6 is disposed within buffer ring 8, which is then disposed within hollow cap 60. Hollow cap 60 is then affixed to a bezel setting 62 or similar plate, which has a screw post 66 that is rotatably insertable into a threated slot 68 in ring 64. In some embodiments, one or more spacers can be included on either side of RFID tag 6 disposed within buffer ring 8. The one or more spacers can be either substantially permissive or substantially inhibiting, as described above.

In some embodiments, shown in FIG. 7, a ring 72 has a channel 74 through its top portion. In some embodiments, the channel 74 is cylindrical and includes a notch 76 cut the full circumference of the channel 74. Channel 74 is sized to hold RFID tag 6 disposed within buffer ring 8. Notch 76 is sized to hold bottom retainer 78 in place. Bottom retainer 78 is formed from a flexible material, such as semi-rigid plastic, so it can be inserted and removed from notch 76. The diameter of bottom retainer 78 is larger than the diameter of channel 74 but smaller than the diameter of notch 76, allowing bottom retainer 78 to be held in place when inserted into notch 76. With bottom retainer 78 inserted into notch 76, buffer ring 8 and RFID tag 6 are disposed within channel 74 and sealed in place by cap 79.

Cap 79 may be connected to ring 72 by cement, glue, solder, or another adhesive.

As with cap 2, cap 79 is formed from a gemstone, a synthetic or imitation gemstone, or like material including glass or plastic. Also, cap 79 defines a convex, substantially hemispherical surface and a flat surface. In an alternative embodiment, cap 72 may define a concave surface and a flat surface.

In some embodiments, bottom retainer 78 is formed from a material that is substantially permissive of radio frequency transmission and cap 79 is formed from a material that substantially inhibits radio frequency transmissions. In this embodiment, the effective transmission range of RFID tag 6 is greatly limited.

Figure 8A:
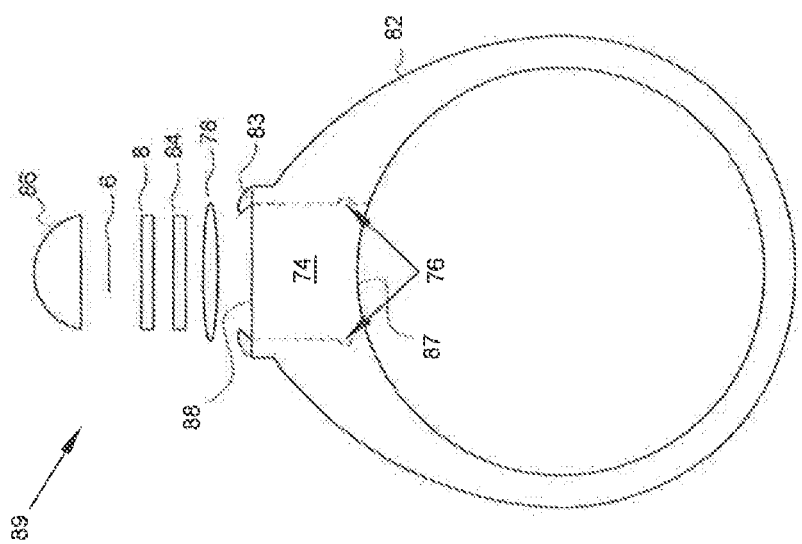

In some embodiments, shown in FIGS. 8A and 8B, a jewelry piece 89 comprises an annular body 82 having a channel 74 with a protruding edge 83 that retains elements disposed within channel 74. When disposed within channel 74, cap 86 is prevented from exiting channel 74 by protruding edge 83. Cap 86, RFID tag 6, buffer ring 8, battery 84, and bottom retainer 78 are loaded from inner side 87 of channel 74 and retained on outer side 88 of channel 74 by protruding edge 83. In some embodiments, channel 74 may be cylindrical and include a notch 76 cut the full circumference of channel 74. Channel 74 may be sized to hold RFID tag 6 disposed within buffer ring 8. Notch 76 is sized to hold bottom retainer 78 in place. Bottom retainer 78 is formed from a flexible material, such as a semi-rigid polymer, so it can be inserted and removed from notch 76. The diameter of bottom retainer 78 is larger than the diameter of channel 74, but smaller than the diameter of notch 76, allowing bottom retainer 78 to be held in place when inserted into notch 76. With bottom retainer 78 inserted into notch 76, buffer ring 8 and RFID tag 6 are disposed within channel 74 and held in place by cap 86. As with cap 2, cap 86 may be formed from a gemstone, a synthetic or imitation gemstone, or like material including glass or plastic. Also, cap 86 may define a convex, substantially hemispherical surface and a flat surface. In alternative embodiments, cap 86 may define a concave surface and a flat surface. In some embodiments, bottom retainer 78 may be replaced with a retaining clip such as retainer clip 50 described above. In some embodiments, battery 84 is omitted and RFID tag 6 may comprise a passive-type tag. In other embodiments, spacers (not shown) are used to ensure RFID tag 6, buffer ring 8, and battery 84 remain immobilized during use. In some embodiments, additional RFID tags are disposed within channel 74; multiple RFID strips are used to increase functionality or security of jewelry piece 89.

Referring to FIGS. 9A, 9B, 9C, and 9D, a ring 90 comprises two raised edges 92 defining a channel 94. A printed RFID strip 96 and decorative cover 104 are disposed within channel 94. In some embodiments, a battery 102 may also be disposed within the channel and operatively connected to RFID strip 96. Ring 90 is formed from stainless steel, precious metal (gold, silver, platinum, and the like), or other materials suitable for forming jewelry, e.g., carbon fiber or titanium alloys. In some embodiments, ring 90 may be formed from various insulating materials such as ceramic, nylon, acrylic, Lexan, or the like, which provide non-radio wave interference properties, allow for low cost of production, low weight, improve esthetics, and can be easy to remove in an emergency.

In some embodiments, a ring formed from ceramic or similar material is given the appearance of a precious metal or other metal through chemical vapor deposition of a metal coating on the exterior surface of the ring. In other embodiments, a ring formed from ceramic or similar material is given the appearance of a precious metal or other metal through ionic beam subsurface deposition of metal below the exterior surface of the ring. Such embodiments have the advantage of appearing as metal rings while having minimal RF interference due to their ceramic construction.

Ring 90 comprises an inner surface 106, an outer surface 108 defined by the top surfaces of raised edges 92, and a channel bottom surface 110. In some embodiments, ring 90 is annularly shaped. RFID strip 96 comprises a flexible substrate or semiconductor which includes at least one memory chip 98 and an antenna 100. In some embodiments, RFID strip 96 includes at least one RFID tag which may be of any suitable type and configuration such as a RFID wafer. In some embodiments, RFID strip 96 includes a printed, flexible CMOS integrated circuit. In some embodiments, battery 102 may be constructed from flexible materials, such as a flexible lithium or graphene battery. In some embodiments, additional RFID strips are disposed within channel 94; multiple RFID strips are used to increase functionality or security of ring 90. Decorative cover 104 is dimensioned to fit into channel 94, and formed from a gemstone, a synthetic or imitation gemstone, or like material including glass or plastic. In some embodiments, decorative cover 104 may be formed from a thermo-reactive material which changes color based on temperature. Decorative cover 104 may take many shape suitable for decorative and functional purposes. In some embodiments, decorative cover 104 may be connected to raised edges 92 by cement, glue, solder, or other suitable adhesive. In other embodiments, decorative cover 104 may be connected to raised edges 92 by friction fitting. In further embodiments, an exterior surface 112 of decorative cover 104 may be seated flush with outer surface 108 of ring 90. In yet further embodiments, decorative cover 104 may be formed over RFID strip 96 and battery 102. In many embodiments, decorative cover 104 is operatively connected to battery 102 and comprises solar power cells to charge the batter 102 with solar-generated electricity. In some embodiments, decorative cover 104 includes LED panels which are configured to display information to a user. For example, the panels may be configured to display messages regarding the status of the system, such as "00S" indicating the system is out of service or "Low Bat" indicating the battery power is about to run out of power. As another example, LED panels may be configured to display various parameters to a user such as time, date, temperature, or user's pulse.

Figure 9C:
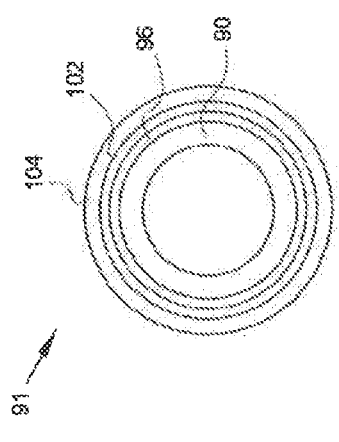
FIGS. 9A, 9B, 9C, and 9D are schematic cross-sectional views of an example of a jewelry piece with an interchangeable radio frequency identification tag in accordance with some embodiments of the invention.
Figure 9D:
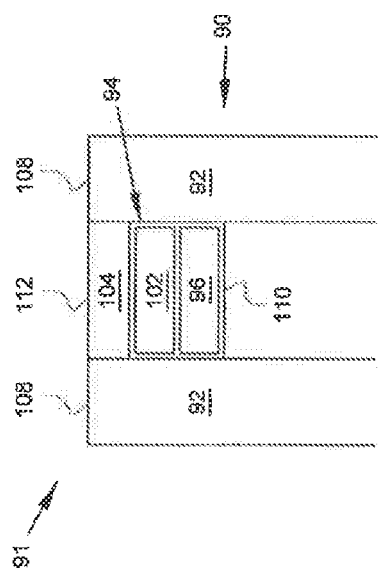
Figure 9A:
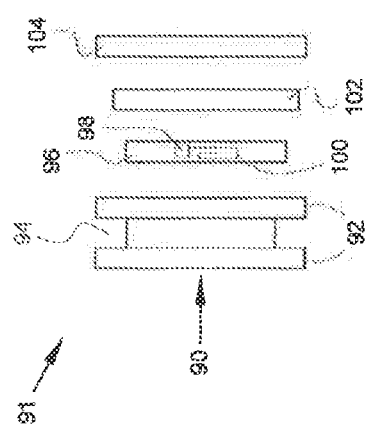
Figure 9B:
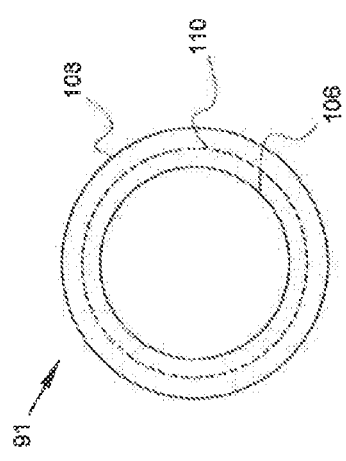

RFID strip 96 may be disposed on top of channel bottom surface 110, with battery 102 disposed above and operably connected to RFID strip 96. Decorative cover 104 is disposed above battery 102 and, in many embodiments without a battery 102, above RFID strip 96. In some embodiments, spacers (not shown) are used to ensure RFID strip 96 and/or batter 102 remain immobilized during use. Referring to FIG. 9D an assembled jewelry piece 91 includes an RFID strip 96 and battery 102 disposed between raised edges 92, channel bottom surface 110, and decorative cover 104. Exterior surface 112 of decorative cover 104 sits flush with outer surface 108 of ring 90.

In some embodiments, a plurality of nanocapacitors may be applied to the surface of or integrated with the material forming ring 90. In some embodiments, the nanocapacitors are graphene nanocapacitors. In some embodiments, the nanocapacitors are formed as disclosed in U.S. Patent Application Publication 2013/0224394, the entirety of which is herein incorporated by reference. The nanocapacitors are configured to absorb ambient energy, such as solar energy or thermal energy from the user, and convert it to electrical energy to be used by RFID strip 96.

In each of the embodiments presented above a sealant may be used between components to create a sealed chamber containing the RFID tag. For example, in the jewelry piece 100 presented in FIG. 1, a sealant may be used between cap 2 and housing 14. As another example, a sealant may be used between the decorative cover 104 and ring 90 of jewelry piece 91 presented in FIGS. 9A, 9B, 9C, and 9D. In some embodiments, the sealant may be silicon-based, in other embodiments the sealant may be an epoxy sealer.

In some embodiments of the present disclosure, a portion or all of the exterior surface of the jewelry piece is finished with a scratch resistant coating such as certain ceramics, diamond chemical vapor deposition, or the like. Further, in some embodiments, each component disclosed above which includes at least one exterior surface of the jewelry piece is formed from ceramic, glass, gemstone, carbon fiber composite, solar cell, LED screen, diamond chemical vapor deposition, or any combination thereof.

The use of RFID tags has spread to innumerable applications, and embodiments of the present disclosure can be applied in numerous ways. In general use, a RFID tag is read by an RFID reader to transfer data on the tag to the reader. The RFID reader is operatively connected to a computer or other processing system and transfers data from the tag to the computer or processing system for use.

By way of example, RFID tags can be used in a key fob to provide keyless locking and unlocking of a vehicle door. The RFID tag enclosed in the fob uniquely identifies the key associated with a given vehicle. As a driver approaches the vehicle door, a RFID reader located in the door handle, door, or elsewhere in the vehicle reads the identifying information contained on the RFID tag. A processing system uses this identifying information to determine if the key fob is associated with the vehicle and should thus be granted access to the vehicle. If the key fob is positively associated with the vehicle, the processing system sends a signal to the vehicle door to unlock.

Additional uses of the present disclosure are included in Table 1. Table 1 assumes the implementation device (i.e.—vehicle) is equipped with a RFID reader and associated circuitry. The examples in Table 1 are provided for illustrative purposes and are in no way meant to be a full list of potential applications of the present disclosure.

TABLE 1

Applications of the Present Disclosure

Keyless starting of a vehicle
Arming or disarming a security system
Opening, locking, or unlocking a residential or commercial door, gate, or equivalent
Opening, locking, or unlocking a safe
Enabling operation of a firearm
Payment using credit or debit card information loaded into RFID tag
Opening, locking, unlocking, or starting a personal watercraft, motorcycle, or machinery
Enabling use of a cellular telephone
Verifying identity at an airport or security checkpoint
Verifying identity, license, insurance status, and vehicle registration during a traffic stop The jewelry piece with interchangeable RFID tag disclosed above has several advantages. A jewelry piece provides a convenient and unobtrusive way to carry an RFID tag and is less likely than a badge, key fob, or other RFID tag carrier to be lost or damaged. By making the RFID tag interchangeable through the various means disclosed above, the jewelry piece provides a flexibility to the user to carry with them a range of information. For example, a user can have a jewelry piece with a command module containing an RFID tag loaded with identifying information specific to their professional life, i.e. containing login information for their work computer, access information to their office, etc. That same user could then switch command modules, outfitting the jewelry piece with a second command module loaded with personal information such as identifying information for specific use at a doctor's office. In various circumstances, a user could chose to limit the data they carry within their jewelry piece so as to limit the potential for fraud and identity or information theft. Command modules could also be exchanged for purely aesthetic purposes.

As yet another advantage of the invention, the jewelry piece with interchangeable RFID tag may be an entirely covert means of carrying information. As will be known to those skilled in the art, RFID transceivers and their associated circuitry are capable of securely storing a substantial amount of information. As disclosed above, this circuitry may also monitor and provide real-time information such as time, date, temperature, or user's pulse. The information contained in the RFID tag may be carried within the jewelry piece and is thus be concealed from public view.

In some embodiments, an apparatus for conveniently carrying a radio frequency identification tag comprises a jewelry piece including a threaded slot for receiving a screw post; a cap with a convex, substantially hemispherical surface and a flat surface, the flat surface connected to a housing including the screw post; a radio frequency identification tag, disposed within a buffer ring which is disposed within the housing; and wherein the housing is operatively connected to the jewelry piece by rotatably inserting the screw post in the threaded slot.

In some embodiments, an apparatus for carrying a radio frequency identification tag within a jewelry ring comprises a jewelry ring including a threaded slot; a bezel setting comprising a flat plate and a screw post, wherein the bezel setting is operatively connected to the jewelry ring by rotatably inserting the screw post into the threaded slot; a cap comprising a convex, substantially hemispherical surface and a flat surface including a recess, and wherein the flat surface is connected to the bezel setting; and a radio frequency identification tag, disposed within a buffer ring which is disposed within the recess of said cap.

In some embodiments, an apparatus for carrying a radio frequency identification tag within a jewelry ring comprises a jewelry ring including a threaded recess; a cap comprising a substantially hemispherical portion and a threaded member portion; and a radio frequency identification tag, disposed within a buffer ring, the buffer ring disposed within the threaded recess wherein the threaded recess encloses the radio frequency identification tag and the buffer ring when the cap is rotatably inserted into the threaded recess. A wearable electronic device 200 according to another embodiment of the invention is shown in FIGS. 10-17 and 21. The wearable electronic device 200 has a ring body 210, a substrate 240, a battery 270, an inductive layer 280, and a shielding layer 290. The major components of the wearable electronic device 200 will now be described in greater detail.

Figure 10:
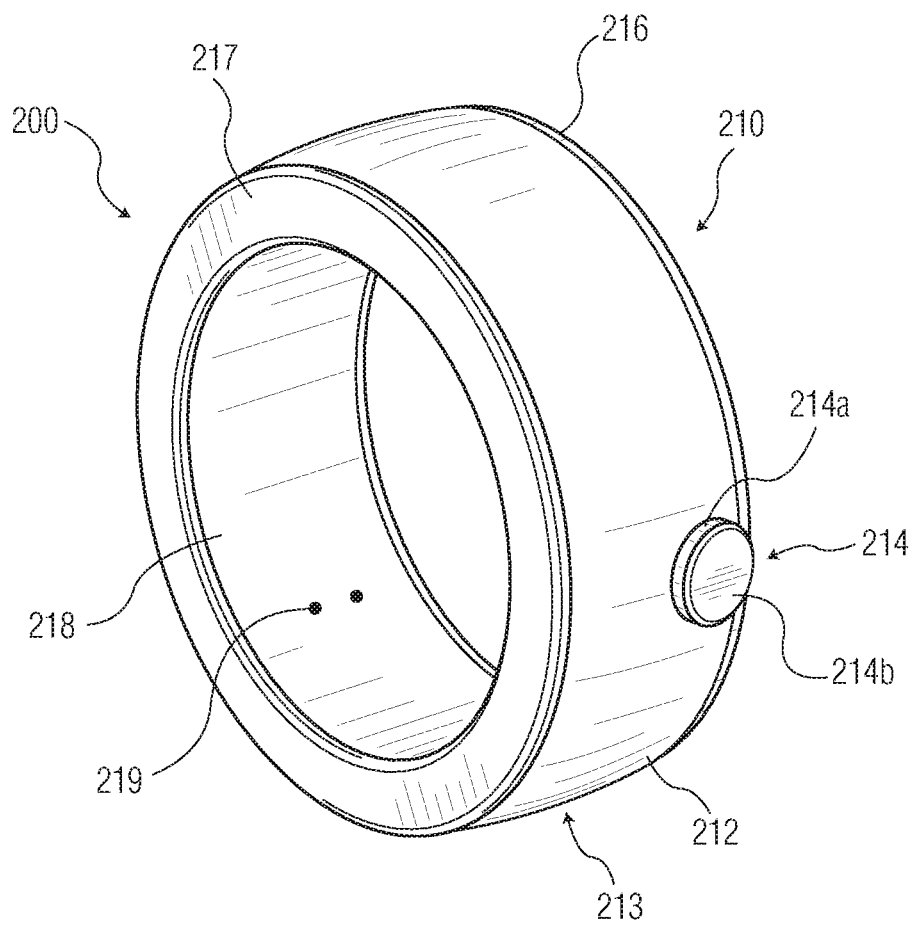
FIG. 10 is perspective view of a wearable electronic device according to an embodiment of the invention.
Figure 12:
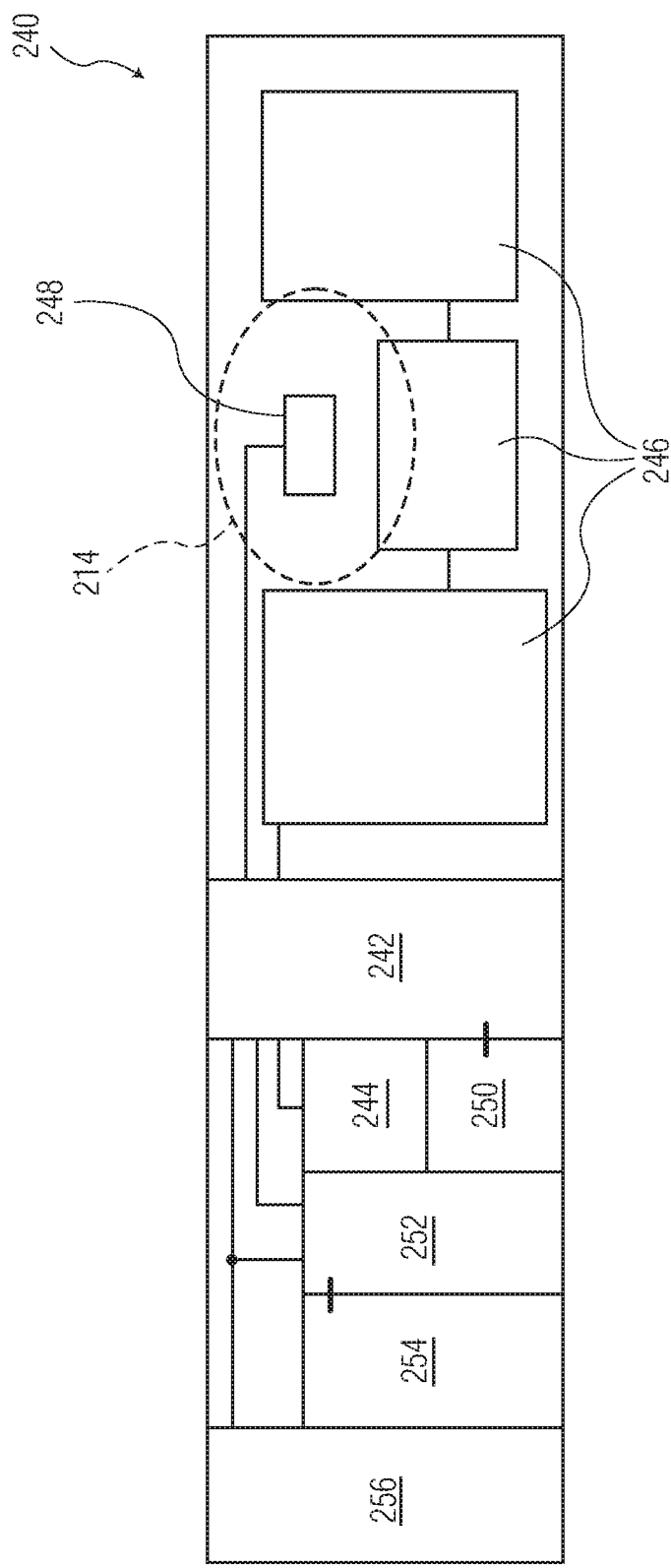
FIG. 12 is a schematic view of a substrate of the wearable electronic device of FIG. 10.
Figure 13:
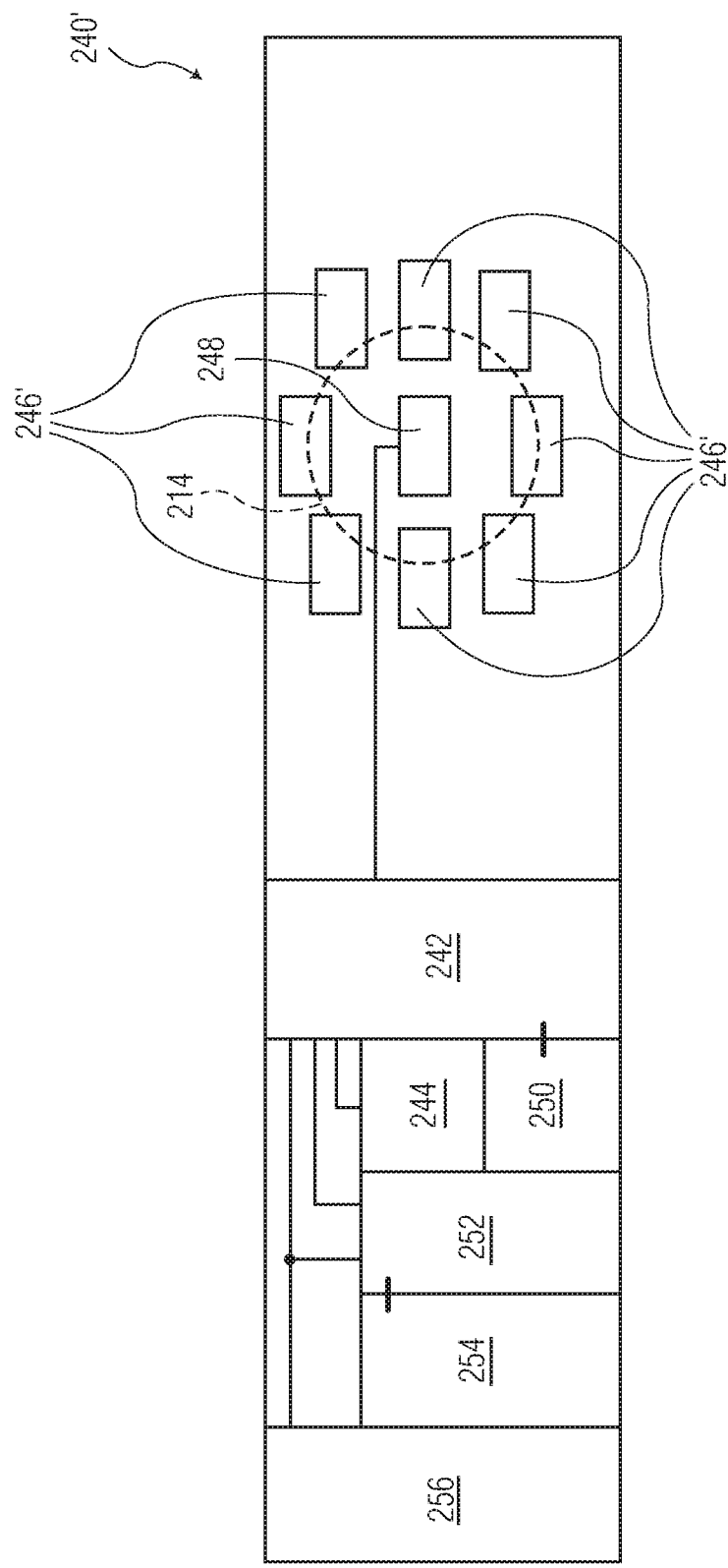
FIG. 13 is a schematic view of another substrate of the wearable electronic device of FIG. 10.

The ring body 210 is shown in FIGS. 10, 12, and 13, and includes an outer cover 212, an interface 214, a first side cover 216, a second side cover 217, and a sizing insert 218.

Figure 11:
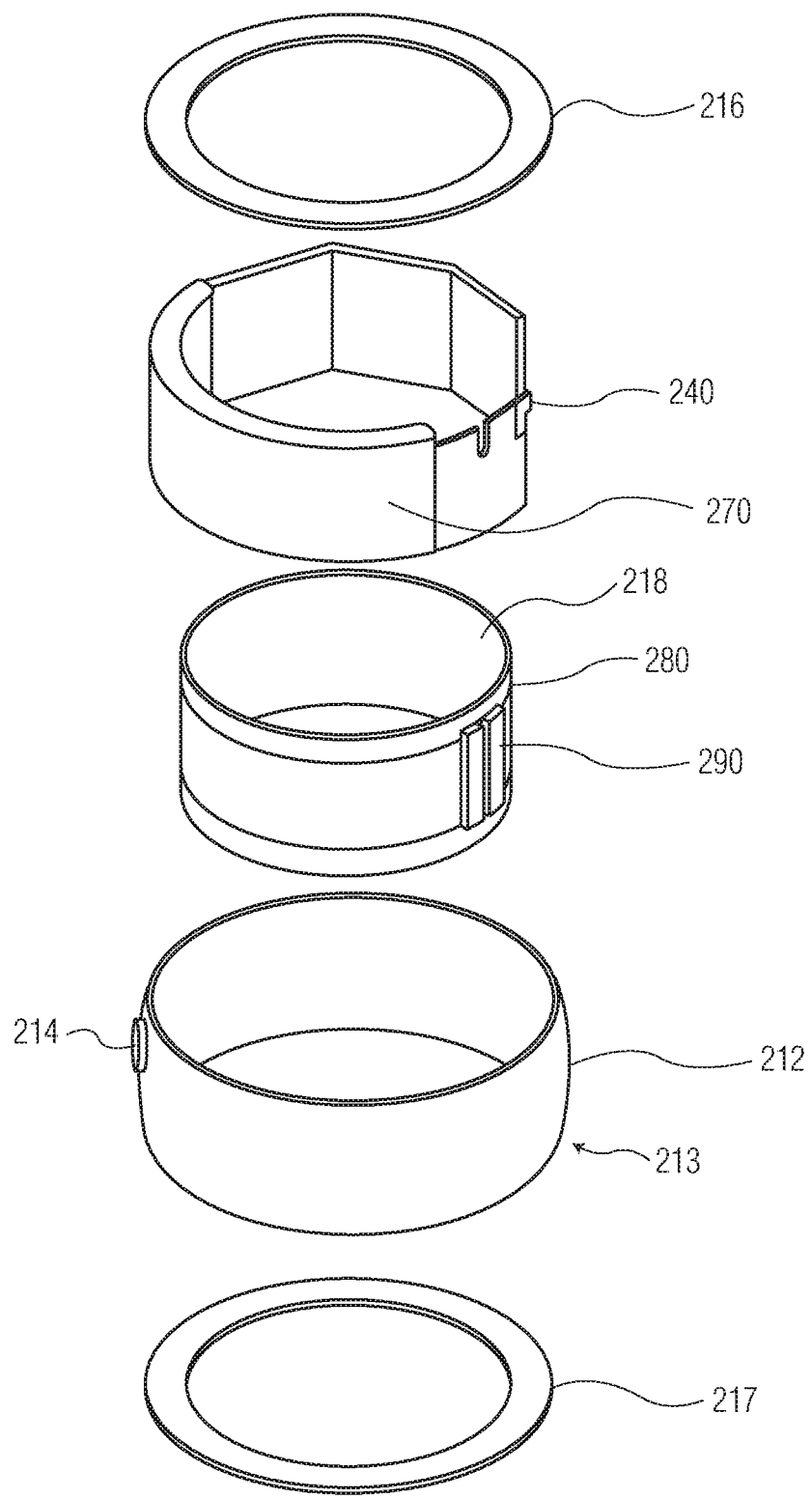
FIG. 11 is an exploded view of the wearable electronic device of FIG. 10.
Figure 15:
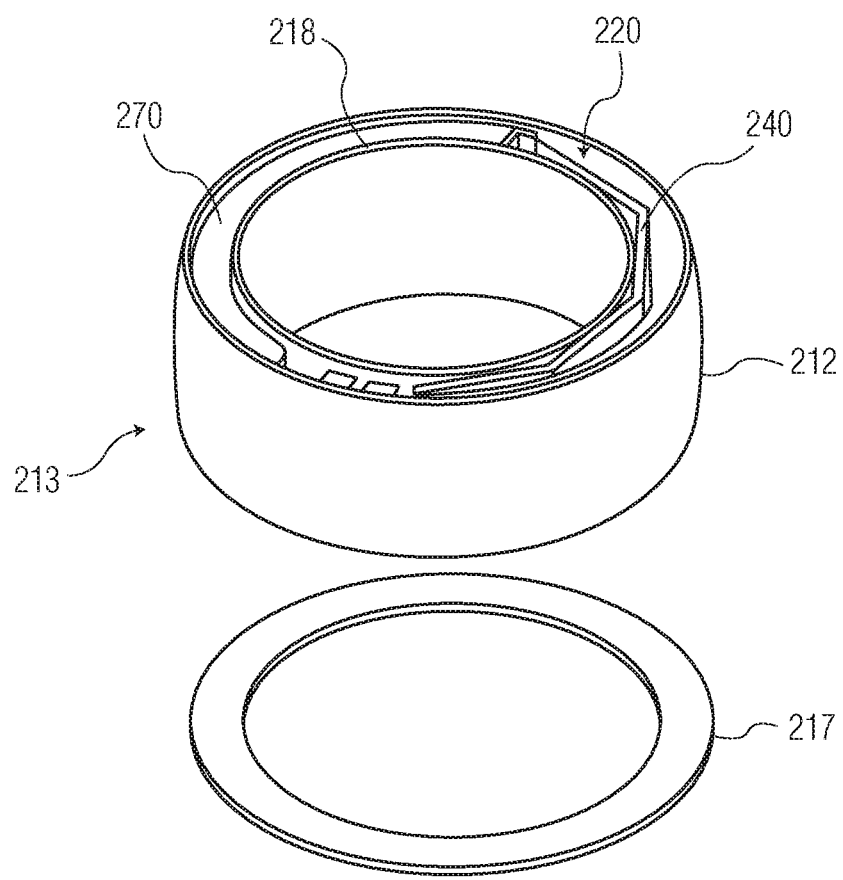
FIG. 15 is an exploded view of the wearable electronic device of FIG. 10.

The outer cover 212, as shown in FIGS. 10, 11, and 15 is an annular member. The outer cover 212 may be formed from glass, a plastic material such as acrylic glass, a gemstone, a synthetic or imitation gemstone, or a ceramic material. In some embodiments, the material of the outer cover 212 includes a plurality of nanocapacitors 213 applied to the surface of or integrated with the material forming the outer cover 212. The nanocapacitors 213 may be graphene nanocapacitors. The nanocapacitors 213 are configured to absorb ambient energy, such as solar energy or thermal energy from the user, and convert it to electrical energy. The interface 214 is disposed on an exterior of the outer cover 212 and may be located toward one side of the outer cover 212, as shown in FIGS. 10 and 11.

As shown in FIG. 10, the interface 214 has a raised portion 214a protruding from the exterior of the outer cover 212 to an interface surface 214b. In the shown embodiment, the interface surface 214b is circular and the raised portion 214a is consequently cylindrical. One with ordinary skill in the art would appreciate that the interface surface 214b may alternatively have a variety of shapes, including a square or a rectangle. The interface 214 may be formed from a plastic, glass, or metal material.

The first side cover 216 and the second side cover 217, as shown in FIGS. 10 and 11, are annular members formed from a plastic material. In the shown embodiment, the first side cover 216 and the second side cover 217 are identically shaped.

The sizing insert 218, as shown in FIGS. 10 and 11, is an annular member which may be formed from a metal, a plastic, or may be a plastic filled with carbon. In the shown embodiment, the sizing insert 218 has a plurality of insert passageways 219 extending through the sizing insert 218.

The substrate 240 is shown in FIGS. 11-14. In the shown embodiment, the substrate 240 is a flexible printed circuit board. As would be appreciated by one with ordinary skill in the art, the substrate 240 may alternatively be a shaped, rigid printed circuit board. The substrate 240 has disposed thereon a processor 242, a memory 244, a plurality of capacitive plates 246, a light emitting diode (LED) 248, an accelerometer 250, a communication module 252, an antenna 254, and a battery management module 256.

The processor 242 may be any form of processor known to those with ordinary skill in the art. The memory 244 is connected to the processor 242 and is a non-transitory computer readable medium storing software instructions executable by the processor 242.

The plurality of capacitive plates 246 are flat members disposed on the substrate 240 which store electrical energy.

The plurality of capacitive plates 246 are each connected to the processor 242, and each send a signal to the processor 242 indicating a change in a stored capacitance value.

The LED 248 may be any form of LED known to those with ordinary skill in the art, such as an RGB LED. The LED 248 is connected to the processor 242 and controlled by the processor 242 to illuminate in a range of colors with various frequencies and various durations.

As shown in FIG. 12, the plurality of capacitive plates 246 may be arranged linearly and equidistant from one another along the substrate 240, with the LED 248 disposed centrally among the plurality of capacitive plates 246. In an alternative embodiment of a substrate 240' shown in FIG. 13, the plurality of capacitive plates 246' may be arranged equidistant from one another and encircling the LED 248.

The accelerometer 250, in the shown embodiment, is a three-axis micro electro-mechanical system (MEMS) accelerometer, but as would be appreciated by one with ordinary skill in the art, may be a single-axis or two-axis accelerometer. The accelerometer 250 is connected to the processor 242 and sends a signal to the processor 242 indicating acceleration along each of axes of the accelerometer 250.

The communication module 252 is a device capable of wirelessly communicating data over short distances. The communication module 252 may, for instance, be a device communicating using short-wavelength radio waves, such as a Bluetooth device. In the shown embodiment, the communication module 252 is a Bluetooth low energy device having a communication range of at least ten meters. The communication module 252 is connected to the processor 242 and the antenna 254, and transmits and receives data externally of the wearable electronic device 200 via the antenna 254. The antenna 254 may be any form of antenna 254 known to those with ordinary skill in the art, and may be printed on the substrate 240. The antenna 254 may be formed of a conductive material, such as copper, gold, graphene, or other antenna materials known to those with ordinary skill in the art.

The battery management module 256 is connected to the processor 242 and the communication module 254. The battery management module 256 receives power and distributes power to the processor 242 and the communication module 252 within the substrate 240.

The battery 270 is shown in FIGS. 11, 14, 15, and 16. In the shown embodiment, the battery 270 is a flexible lithium-ion battery. The battery 270 may alternatively be rigid, and/or may be an aluminum-ion battery, an alkaline battery, or other type of battery known to those with ordinary skill in the art.

Figure 16:
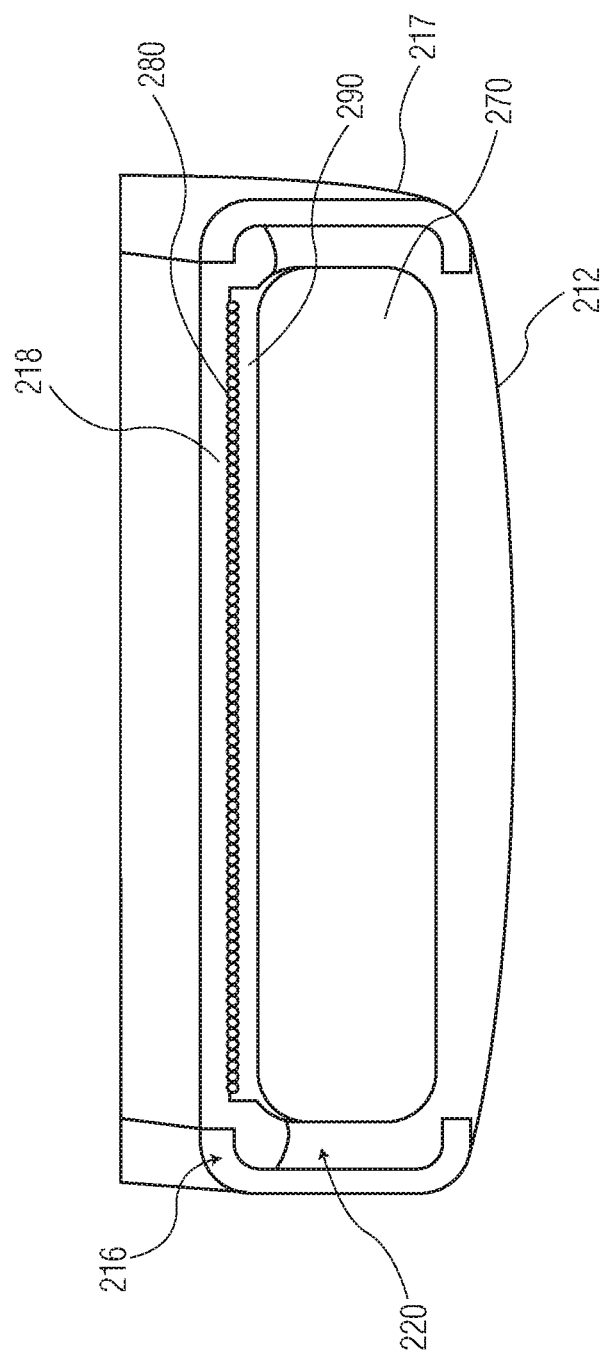
FIG. 16 is a sectional view of the wearable electronic device of FIG. 10.

The inductive layer 280 and the shielding layer 290 disposed on the sizing insert 218 are shown in FIGS. 11 and 16. The inductive layer 280 is formed of a material capable of receiving an inductive charge, such as copper, aluminum, graphene, or other materials capable of receiving an inductive charge known to those with ordinary skill in the art. In the shown embodiment, the inductive layer 280 is formed as a coil disposed on the sizing insert 218, but the inductive layer 280 could alternatively be printed on the sizing insert 218. The shielding layer 290 comprises a magnetic shielding material, such as a metal material.

The assembly of the wearable electronic device 200 will now be described in greater detail with reference to FIGS. 11-16.

Figure 14:
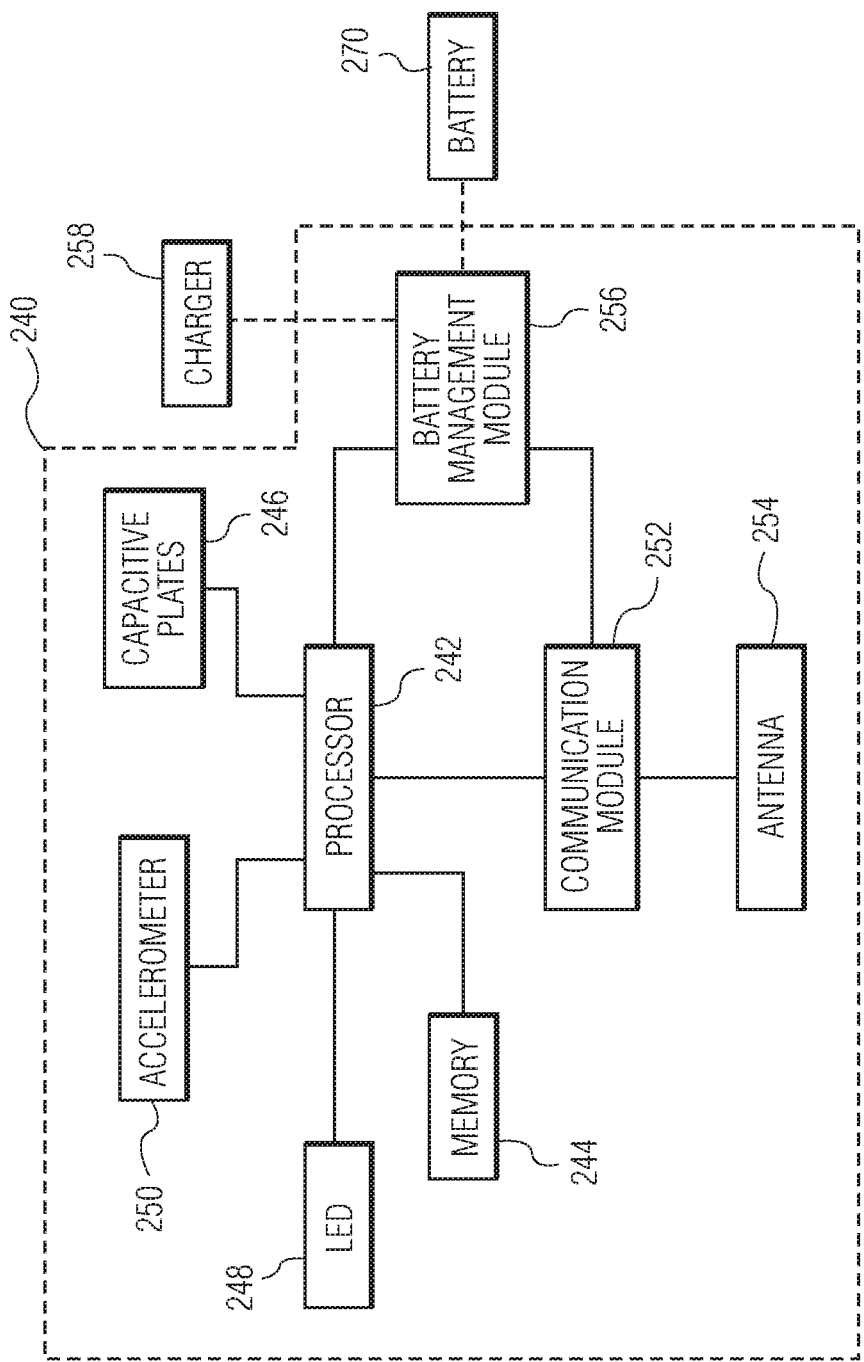
FIG. 14 is a block diagram of components of the substrate shown in FIG. 12.

The battery 270 is electrically connected to the substrate 240 at the battery management module 256, as shown in FIGS. 11 and 14, and provides power to the substrate 240. The connected battery 270 and substrate 240 are bent or otherwise positioned within the outer cover 212, as shown in FIG. 15. The substrate 240 is positioned within the outer cover 212 such that, as shown in FIGS. 12 and 13, the interface 214 is aligned with the LED 248 and is positioned proximate the plurality of capacitive plates 246, aligned with a center of the plurality of capacitive plates 246. The interface 214 may overlap a portion of the plurality of capacitive plates 246.

As shown in FIGS. 11 and 16, the inductive layer 280 is disposed circumferentially around an exterior of the sizing insert 218, and the shielding layer 290 is disposed circumferentially around the inductive layer 280. The sizing insert 218 having the inductive layer 280 and the shielding layer 290 disposed thereon is positioned within the battery 270 and substrate 240, as shown in FIG. 15.

The first side cover 216 and the second side cover 217 are attached to opposite ends of the outer cover 212 and the sizing insert 218, as shown in FIGS. 10, 11, and 16, using an adhesive, such as a silicone adhesive, an epoxy, or other adhesives known to those with ordinary skill in the art. An exterior edge of the first side cover 216 is attached to a first end of the outer cover 212, and an interior edge of the first side cover 216 is attached to a first end of the sizing insert 218. An exterior edge of the second side cover 217 is attached to an opposite second end of the outer cover 212, and an interior edge of the second side cover 217 is attached to an opposite second end of the sizing insert 218. The assembly of the ring body 210 including the outer cover 212, the sizing insert 218, the first side cover 216, and the second side cover 217 thus defines an annular receiving space 220 within the ring body 210 in which the substrate 240, battery 270, inductive layer 280, and shielding layer 290 are disposed.

The wearable electronic device 200 is charged by a charger 258 shown in FIG. 14. The charger 258 forms an electrical connection with the battery management module 256 and transfers power to the battery management module 256. The battery management module 256 transmits the received power to charge the battery 270, and also distributes power from the battery 270 and charger 258 to the processor 242 and communication module 252. The charger 258 may be a contact charger, with portions of the charger 258 mating with the plurality of insert passageways 219 to contact the battery management module 256. The charger 258 may alternatively be an inductive charger, in which case the charger 258 is inductively coupled to the battery management module 256 via the inductive layer 280 in order to transfer power.

Figure 17:
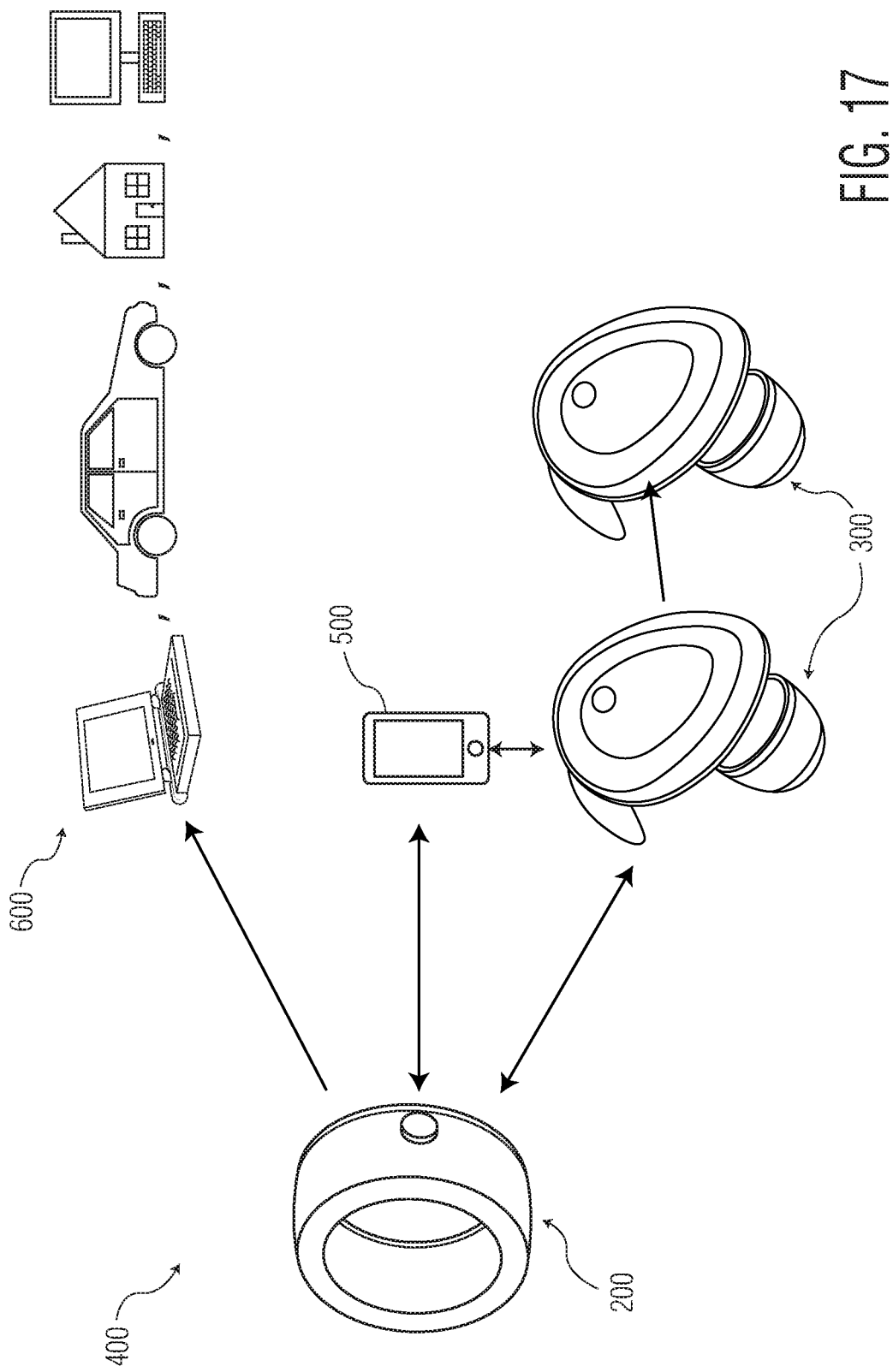
FIG. 17 is a schematic view of a wireless communication system according to the invention.

The wearable electronic device 200 is used within a wireless communication system 400 which, as shown in FIG. 17, may also include a plurality of earbuds 300, a mobile computing device 500, and another device 600.

One of the plurality of earbuds 300 is shown in FIGS. 17-20. The earbud 300 has a housing 310, a substrate 330, a battery 350, a speaker 360, a microphone 370, and a plurality of sensors 380. The major components of the earbud 300 will now be described in greater detail.

Figure 18:
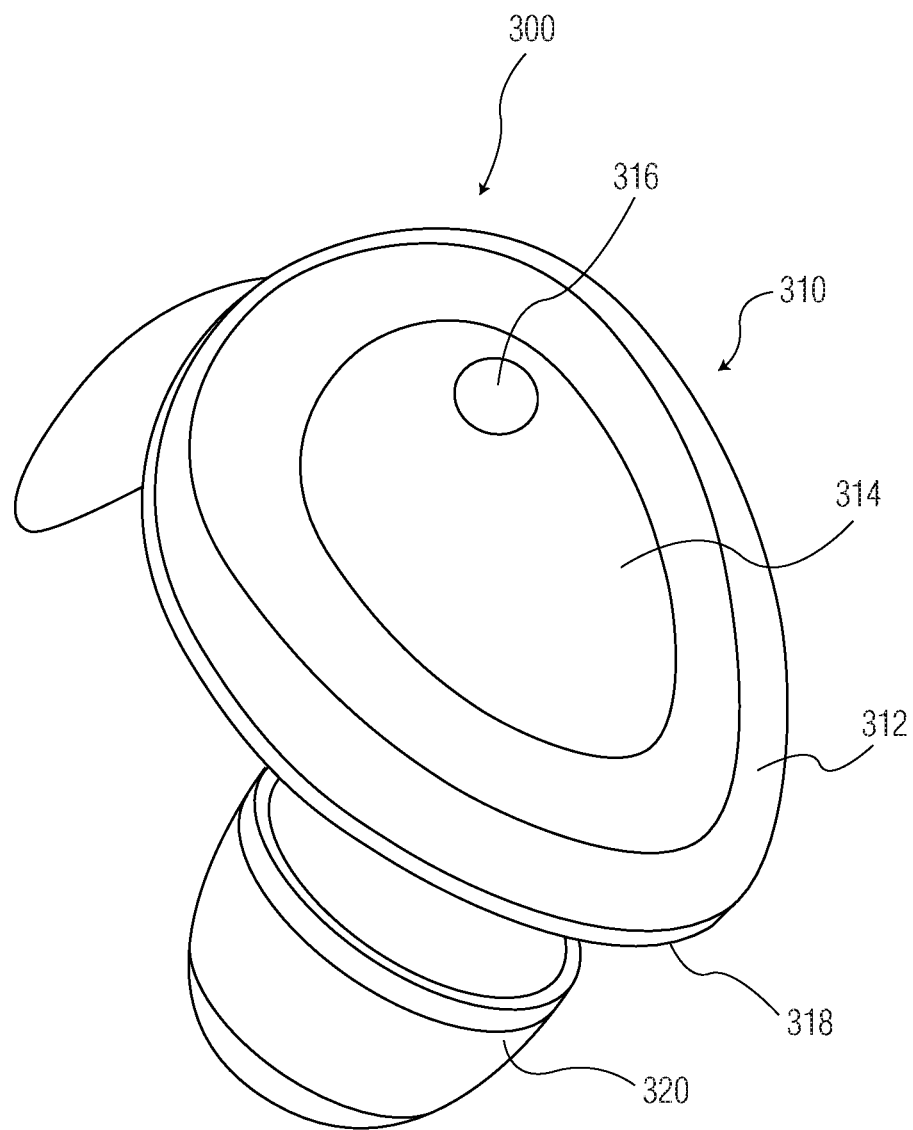
FIG. 18 is a perspective view of an earbud of the wireless communication system of FIG. 17.
Figure 19:
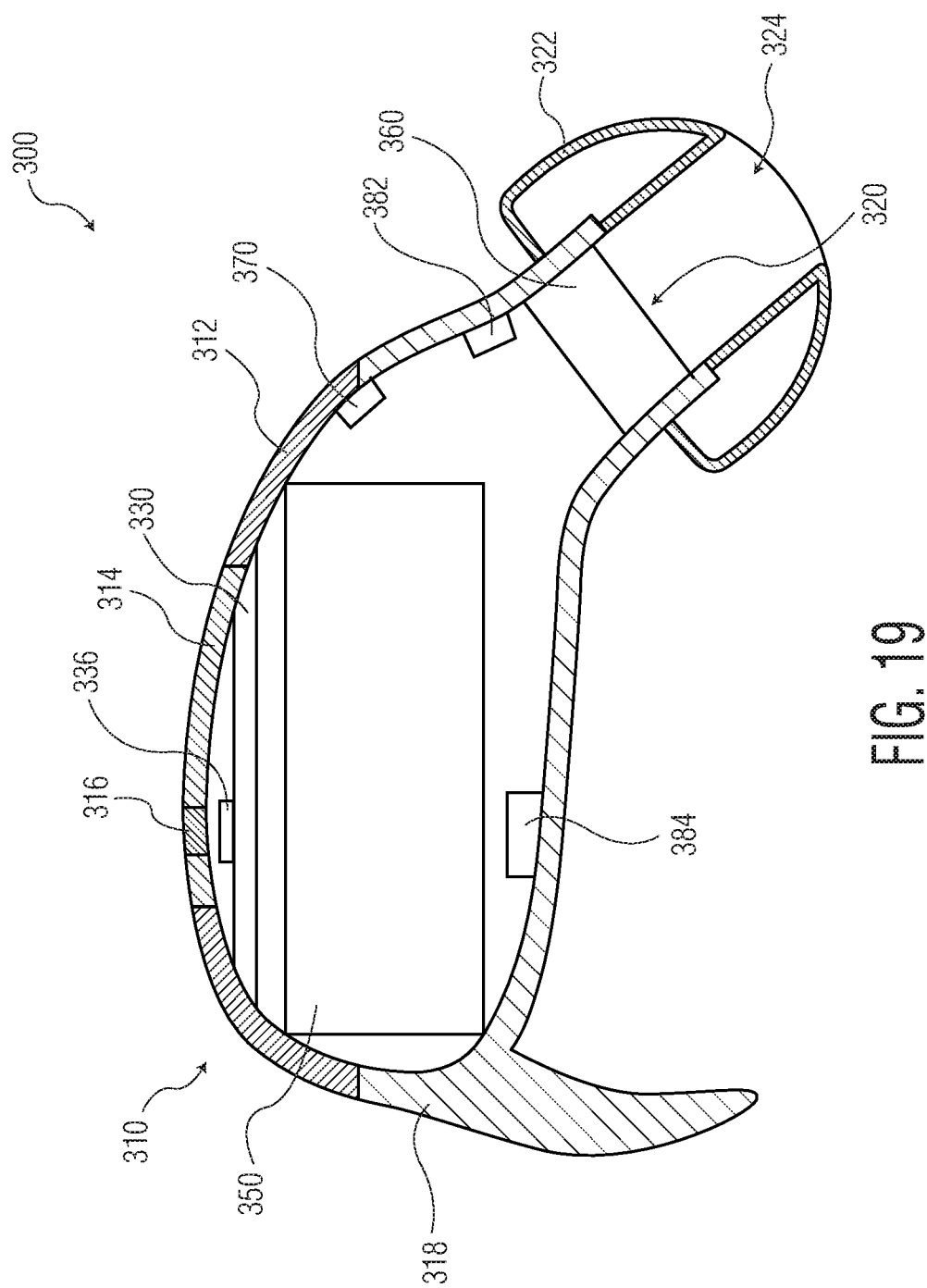
FIG. 19 is a sectional view of the earbud of FIG. 18.

The housing 310 is shown in FIGS. 18 and 19. The housing 310 has an upper cover 312, a lower cover 318, and a dome portion 322.

The upper cover 312, as shown in FIGS. 18 and 19, has a key 314 disposed approximately centrally within the upper cover 312. The key 314 is movable with respect to the rest of the upper cover 312, such as by depression from a user. The key 314 has an indicator 316. In the shown embodiment, the indicator 316 is a transparent circular portion disposed biased from a center of the key 314. As would be appreciated by those with ordinary skill in the art, the indicator 316 may alternatively be translucent, and may be a square, rectangle, or any other shape known to those with ordinary skill in the art. The upper cover 312 is formed of a plastic material.

The lower cover 318, as shown in FIGS. 18 and 19, is formed to be removably positioned in a user's ear. The lower cover 318 is formed of a plastic material, and has a lower cover passageway 320 formed at one end.

The dome portion 322 is shaped to fit in a user's ear canal and has a dome passageway 324 formed at one end. The dome portion 322 is formed of a plastic material.

Figure 20:
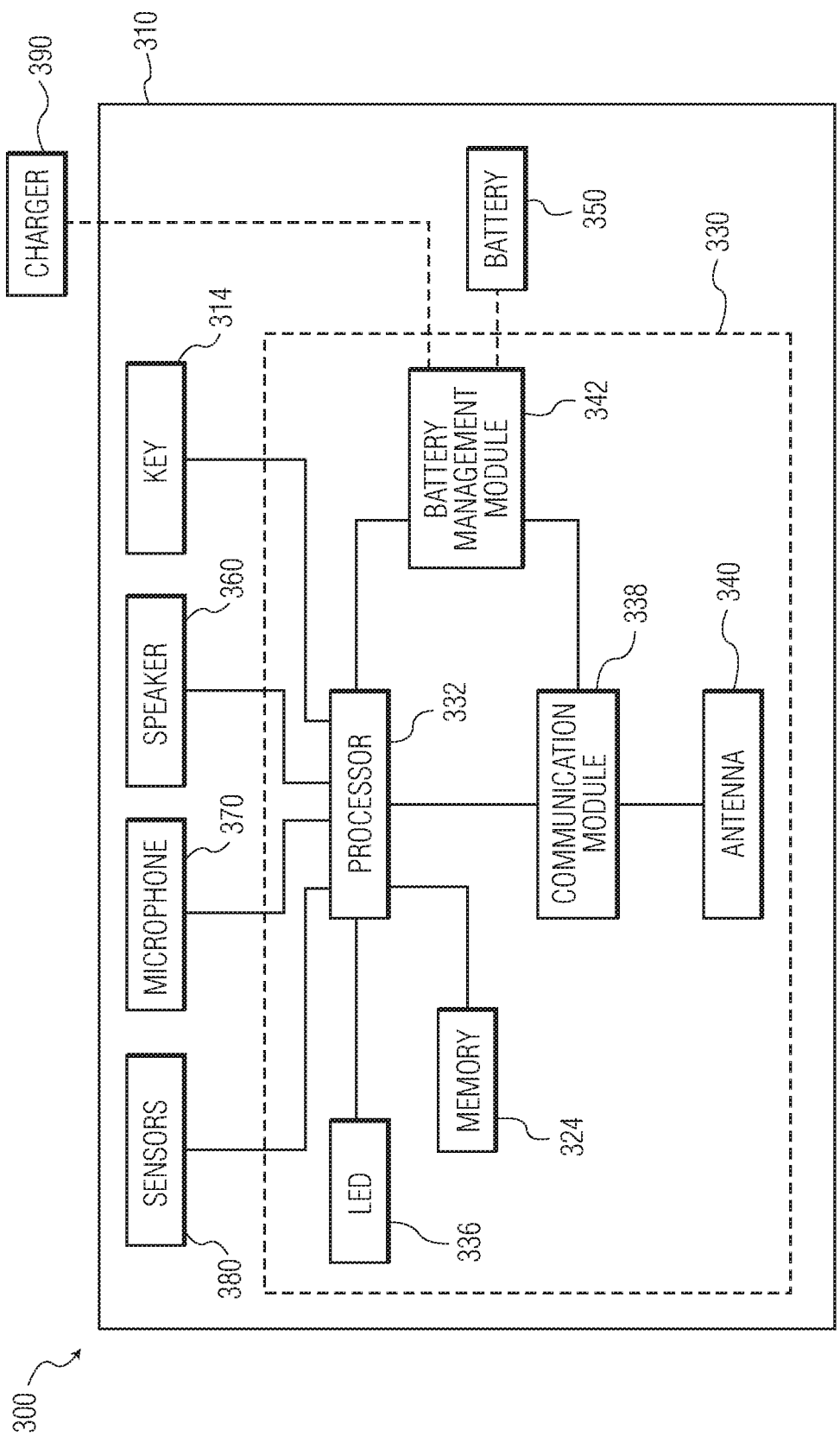
FIG. 20 is a block diagram of the earbud of FIG. 18.

The substrate 330 is shown in FIGS. 19 and 20. In the shown embodiment, the substrate 330 is a flexible printed circuit board. As would be appreciated by one with ordinary skill in the art, the substrate 330 may alternatively be a shaped, rigid printed circuit board. The substrate 330 has disposed thereon a processor 332, a memory 334, a light emitting diode (LED) 336, a communication module 338, an antenna 340, and a battery management module 342.

The processor 332 may be any form of processor known to those with ordinary skill in the art. The memory 334 is connected to the processor 332 and is a non-transitory computer readable medium storing software instructions executable by the processor 332.

The LED 336 may be any form of LED known to those with ordinary skill in the art, such as an RGB LED. The LED 336 is connected to the processor 332 and controlled by the processor 332 to illuminate in a range of colors with various frequencies and various durations.

The communication module 338 is a device capable of wirelessly communicating data over short distances. The communication module 338 may, for instance, be a device communicating using short-wavelength radio waves, such as a Bluetooth device. In the shown embodiment, the communication module 338 is a Bluetooth low energy device having a communication range of at least ten meters. The communication module 338 is connected to the processor 332 and the antenna 340, and transmits and receives data externally of the earbud 300 via the antenna 340. The antenna 340 may be any form of antenna 340 known to those with ordinary skill in the art, and may be printed on the substrate 310. The antenna 340 may be formed of a conductive material, such as copper, gold, graphene, or other antenna materials known to those with ordinary skill in the art.

The battery management module 342 is connected to the processor 332 and the communication module 338. The battery management module 342 receives power and distributes power to the processor 332 and the communication module 338 within the substrate 330.

The battery 350 is shown in FIGS. 19 and 20. In the shown embodiment, the battery 350 is a flexible lithium-ion battery. The battery 350 may alternatively be rigid, and/or may be an aluminum-ion battery, an alkaline battery, or any other type of battery known to those with ordinary skill in the art. The battery 350 is electrically connected to the substrate 310 at the battery management module 342, as shown in FIG. 20, and provides power to the substrate 310.

The speaker 360 is shown in FIGS. 19 and 20. The speaker 360 may be any type of audio speaker known to those with ordinary skill in the art. The speaker 360 is connected to the processor 332 and outputs audio based on signals received from the processor 332.

The microphone 370 is shown in FIGS. 19 and 20. The microphone 370 may by any type of microphone known to those with ordinary skill in the art. The microphone 370 is connected to the processor 332 and transmits signals to the processor 332 based on audio received at the microphone 370.

The plurality of sensors 380 are shown in FIGS. 19 and 20 and may include a heartrate sensor 382 and a body temperature sensor 384. The heartrate sensor 382 detects a heartrate of a user and transmits signals to the processor 332 indicative of the user's heartrate. The body temperature sensor 384 detects a body temperature of a user and transmits signals to the processor 332 indicative of the user's body temperature.

The assembly of the earbud 300 will now be described in greater detail with reference to FIGS. 18 and 19. The substrate 330 is fixed to the upper cover 312 and is positioned such that the LED 336 is aligned with the indicator 316. The substrate 330 is also connected to the key 314 such that movement of the key 314 transmits a signal to the processor 332. As shown in FIG. 19, the battery 350, speaker 360, microphone 370, and plurality of sensors 380 are disposed within the housing 310, and the lower cover 318 is attached to the upper cover 312. The dome portion 322 is disposed on the lower cover 318 and the dome passageway 324 aligns with the lower cover passageway 320.

The earbud 300 is charged by a charger 390 shown in FIG. 20. The charger 390 forms an electrical connection with the battery management module 342 and transfers power to the battery management module 342. The battery management module 342 transmits the received power to charge the battery 350, and also distributes power from the battery 350 and charger 390 to the processor 332 and communication module 338. The charger 390 may be a contact charger, with portions of the charger 390 contacting the battery management module 342 to electrically connect with the battery management module 342. The charger 390 may alternatively be an inductive charger, in which case the charger 390 is inductively coupled to the battery management module 342 by an electromagnetic field in order to transfer power.

Mobile computing device 500 shown in FIG. 17 may be any known mobile device executing applications and capable of wireless communication, such as a mobile phone, a tablet computer, or any other mobile devices known to those with ordinary skill in the art.

Other device 600 shown in FIG. 17 may be any other known device capable of wireless communication, such as computers, vehicles, household items, and point of sale (POS) systems.

The use of the wearable electronic device 200 within the wireless communication system 400 will now be described in greater detail with reference to FIGS. 17 and 21-25.

Figure 21:
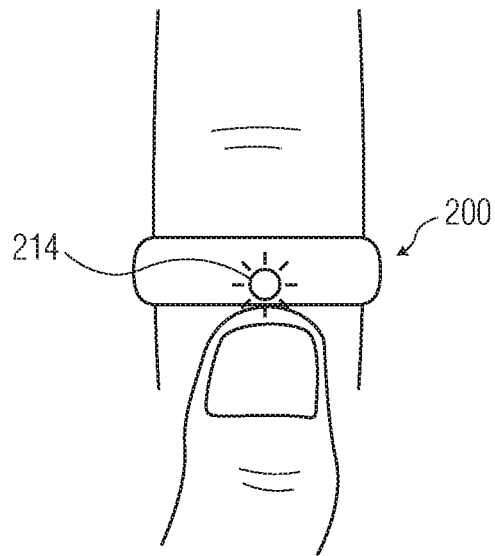
FIG. 21 is a schematic view of the wearable electronic device of FIG. 10 and a user.

The wearable electronic device 200 is shown positioned on a user's finger in FIG. 21. The wearable electronic device 200 is shown positioned such that a user's thumb can access the interface 214, but the wearable electronic device 200 could be positioned on any finger and accessed by any other finger.

Figure 22:
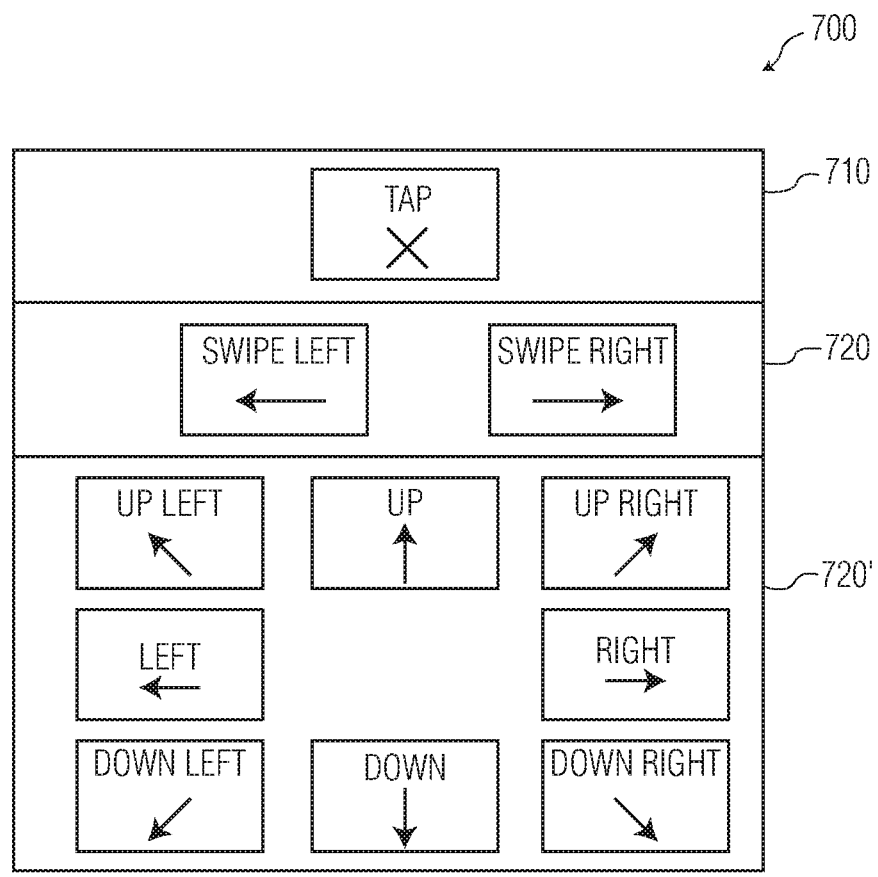
FIG. 22 is a schematic view of gestures of the wearable electronic device of FIG. 10.

The user inputs gestures 700 shown in FIG. 22 to the wearable electronic device 200, which can be transmitted throughout the wireless communication system 400. To input a gesture 700, the user moves a finger in various directions relative to the interface 214. As the user's finger moves over the interface 214, the user's finger is also moving relative to the plurality of capacitive plates 246 positioned within the outer cover 212 around the interface 214. As the user's finger is positioned over or moves with respect to each of the plurality of capacitive plates 246, a stored electrical energy in each capacitive plate of the plurality of capacitive plates 246 changes dependent on the relative position and movement of the user's finger. Each of the plurality of capacitive plates 246 sends a signal indicating a change in the stored electrical energy to the processor 242. The processor 242, executing software stored on the memory 244, compares the relative changes in stored electrical energy of each of the plurality of capacitive plates 246, and based on this information, determines the position and movement of the user's finger corresponding to a gesture 700. The plurality of capacitive plates 246 thus act as a capacitive touch sensor on the wearable electronic device 200.

The gestures 700 shown in FIG. 22 include tap gestures 710 and swipe gestures 720, 720'.

For the tap gestures 710, the user moves his finger only in a vertical direction and touches the interface 214. Variations in the duration of the tap and the number of consecutive taps determine the range of possible tap gestures 710. The tap gestures 710 are the same for both the substrate 240 shown in FIG. 12 and the substrate 240' shown in FIG. 13.

For the swipe gestures 720, 720', the user moves his finger horizontally over the interface 214 in various directions. First swipe gestures 720 are associated with the substrate 240 shown in FIG. 12. In the substrate 240, the plurality of capacitive plates 246 are arranged linearly, and the user can input a swipe left or a swipe right gesture over the interface 214. The number of consecutive swipes and combinations of left and right swipe directions determine the range of possible first swipe gestures 720. Second swipe gestures 720' are associated with the substrate 240' shown in FIG. 13. In the substrate 240', the plurality of capacitive plates 246' are arranged in a circular pattern, and the user can input a swipe left, a swipe right, a swipe up, a swipe down, a swipe diagonal up-left, a swipe diagonal up-right, a swipe diagonal down-right, and a swipe diagonal down-left over the interface 214. The number of consecutive swipes and combinations of swipe directions determine the range of possible second swipe gestures 720'.

Figures 23, 24:
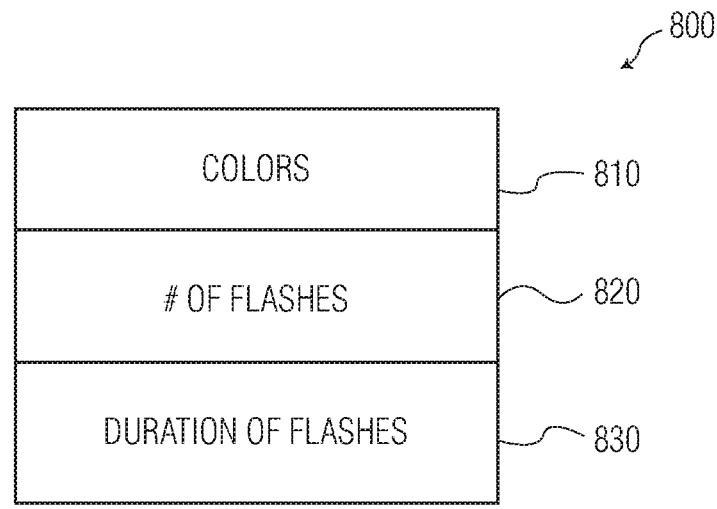
FIG. 23 is a schematic view of notifications of the wearable electronic device of FIG. 10.
FIG. 24 is a schematic view of the gestures of FIG. 22 along with actions and states.

Once the processor 242 determines which gesture 700 the user has input, the processor 242 compares the gesture 700 to a list of user-definable actions 900 for each state 1000 of the wearable electronic device 200, as shown in FIG. 24. The list of user-definable actions 900 correlated with states 1000 of the wearable electronic device 200 and gestures 700 is stored in the memory 244. The processor 242 retrieves the corresponding user-definable action 900, and controls the relevant component to execute the user-definable action 900 associated with the gesture 700 and state 1000. Exemplary user-definable actions 900 and states 1000 of the wearable electronic device 200 associated with gestures 700 will be described in greater detail below.

The wearable electronic device 200 receives notifications 800 shown in FIG. 23 from the wireless communication system 400. The notifications 800 occur at the LED 248 aligned with the interface 214. The notifications 800 can vary in color 810, number of illuminated flashes 820, and duration of each illuminated flash 830. Combinations of colors 810, number of flashes 820, and duration of flashes 830 determine the range of possible notifications 800. The notification 800 light emitted by the LED 248 illuminates at least a portion of the outer cover 212 surrounding the interface 214.

Figure 25:
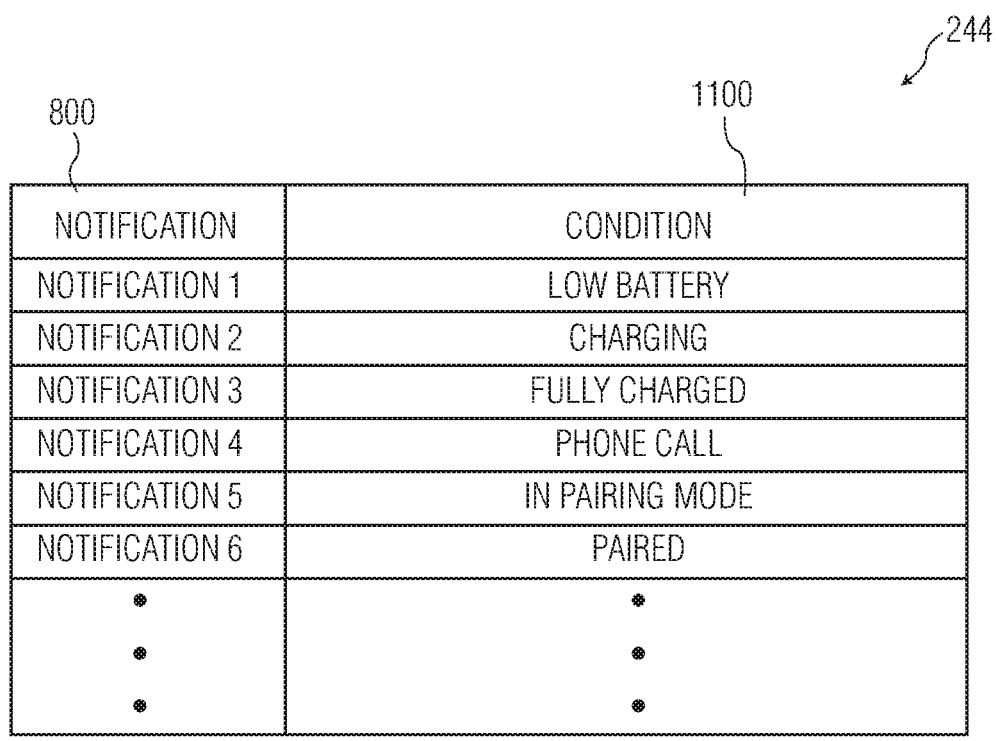
FIG. 25 is a schematic view of the notifications of FIG. 23 along with conditions.

Based on signals received from the wireless communication system 400, described in greater detail below, the processor 242 compares a condition 1100 dictated by the received signals to a list of notifications 800 correlated to conditions 1100 stored in the memory 244 and shown in FIG. 25. The processor 242 retrieves the notification 800 correlated to the condition 1100 and controls the LED 248 to emit the correlated notification 800.

The use of the gestures 700 and notifications 800 within the wireless communication system 400 will now be described in greater detail with reference to FIGS. 17 and 21-25.

A set of notifications 800 can be associated with a state of charge condition 1100 of a state of charge of the battery 270 of the wearable electronic device 200. Notifications 800 may, for example, illuminate the LED 248 to flash 820, 830 a red color 810 when the processor 242 has received a signal indicating that the battery 270 has a low charge, may illuminate the LED 248 a solid red color 810 when the wearable electronic device 200 is connected to the charger 258, and may illuminate the LED 248 a solid white color 810 when the battery 270 is fully charged.

The wearable electronic device 200 is wirelessly connected with the mobile computing device 500 and the plurality of earbuds 300. The wearable electronic device 200 is paired with each of the mobile computing device 500 and one of the plurality of earbuds 300 to initiate the wireless connection.

A set of gestures 700 can be associated with pairing actions 900 for a pairing state 1000. A user inputs a gesture 700 at the interface 214 to initiate wireless pairing, for example, by inputting a single tap 710 of a predetermined duration. Once available for pairing, the communication module 252 of the wearable electronic device 200 connects with the communication module 338 of the earbud 300 and a similar communication module in the mobile computing device 500. The communication module 338 of the earbud 300 and the communication module of the mobile computing device 500 are also connected. The user may input another gesture 700 to initiate a pairing confirmation on a paired device, and may input a further gesture 700 to terminate the wireless pairing, for example, by inputting a single tap 710 of a predetermined duration.

A set of notifications 800 can also be associated with pairing conditions 1100 of the wearable electronic device 200, the earbud 300, and the mobile computing device 500. A notification 800 can indicate that pairing has been initiated, and another notification 800 can indicate that pairing has been completed.

Once connected, the wearable electronic device 200, the earbud 300, and the mobile computing device 500 can wirelessly exchange data via the communication modules 252, 338. The earbud 300 can, for example, transmit data from the plurality of sensors 380 to the mobile computing device 500 via the communication module 338. The wearable electronic device 200 can transmit accelerometer 250 data to the mobile computing device 500 via the communication module 252.

A set of notifications 800 can be associated with correspondence conditions 1100 received at the mobile computing device 500. For example, when the mobile computing device 500 receives an incoming call, the mobile computing device sends a signal to the wearable electronic device 200, which is received by the communication module 252 and sent to the processor 242. The processor 242 compares the received call data to the list shown in FIG. 25 stored in the memory 244, and executes the notification 800 associated with the received call data, for example, by controlling the LED 248 to flash 820, 830 a white color 810. Another notification 800 can be associated with received email correspondence, and a further notification 800 can be associated with received text correspondence.

A further set of notifications 800 can also be associated with known application conditions 1100 executed on the mobile computing device 500. For example, a separate notification 800 can be associated with each of a calendar application alert, a TWITTER alert, an INSTAGRAM alert, and a FACEBOOK alert, among conditions 1100 of other applications known to those with ordinary skill in the art.

Gestures 700 input to the wearable electronic device 200 are determined by the processor 242 and compared to the list of actions 900 and states 1000 shown in FIG. 24. When the action 900 involves either the mobile computing device 500 or the earbuds 300, the processor 242 sends a signal indicating the action 900 to the earbuds 300 and the mobile computing device 500 via the communication module 252. The processor 332 of the earbud 300 and a processor of the mobile computing device 500 receive the signal and control the corresponding components to execute the action 900.

A set of gestures 700 can be associated with notification actions 900 in a notification state 1000. A gesture 700 can be used to toggle notifications 800 on and off, and another gesture 700 can be used to recall previous notifications 800; each of these gestures 700 is determined by the processor 242 and used directly to control the LED 248.

A set of gestures 700 can be associated with phone call actions 900 on the mobile computing device 500 in a phone call state 1000. When a call is incoming, a gesture 700 can be used to reject the call, and another gesture 700 can be used to answer the call. If the call is answered, the audio received at the mobile computing device 500 may be transmitted to the earbuds 300 and played via the speakers 360. The microphone 370 receives audio and transmits the audio back to the mobile computing device 500. During the call, a gesture 700 can be used to increase the volume of the speakers 360, another gesture 700 can be used to decrease the volume of the speakers 360, a further gesture 700 can be used to end the phone call, and an additional gesture 700 can be used to toggle the audio between the earbud 300 and the mobile computing device 500.

A set of gestures 700 can be associated with text message actions 900 on the mobile computing device 500 in a text message state 1000. A gesture 700 can be used to initiate a text message, various gestures 700 can be used to input text into the text message, and a gesture 700 can be used to send the text message.

A set of gestures 700 can be associated with email actions 900 on the mobile computing device 500 in an email state 1000. A gesture 700 can be used to initiate an email message, various gestures 700 can be used to input text into the email message, and a gesture 700 can be used to send the email message.

A set of gestures 700 can be associated music output actions 900 on either the mobile computing device 500 or the earbuds 300 in a music output state 1000. A gesture 700 can be used to play and pause the music, another gesture 700 can be used to increase the volume, another gesture 700 can be used to decrease the volume, another gesture 700 can be used to skip to the next song, and another gesture 700 can be used to skip to the previous song.

A set of gestures 700 can be associated with music input actions 900 on either the mobile computing device 500 or the earbuds 300 in a music input state 100. A plurality of gestures 700 could individually correspond to musical notes output at the mobile computing device 500 or the earbuds 300.

The lists of gestures 700 and notifications 800 described above and shown in FIGS. 24 and 25 are merely exemplary. One with ordinary skill in the art would understand that many other applications and combinations of gestures 700 and notifications 800 are possible.

The wearable electronic device 200 can also communicate other information stored in the memory 242 to external devices.

The wearable electronic device 200 can automatically communicate identification information stored in the memory 242 to external devices. For example, a passcode for the mobile computing device 500 may be stored in the memory 242, and when the communication module 252 is within a communication range of the mobile computing device 500, the processor 242 automatically executes software stored in the memory 242 to transmit the passcode to the mobile computing device 500 via the communication module 252. Whenever the user of the wearable electronic device 200 is within a communication range of his mobile computing device 500, the mobile computing device 500 receives the passcode, compares the passcode to a stored passcode, and automatically unlocks if the passcodes match. The wearable electronic device 200 could similarly unlock other devices 600 shown in FIG. 17 such as computers, vehicles, and household items.

The wearable electronic device 200 can also communicate payment information to external devices. For example, when the communication module 252 is within communication range of a point of sale (POS) system 600, the user can input a gesture 700 to make payment.

Figure 26:
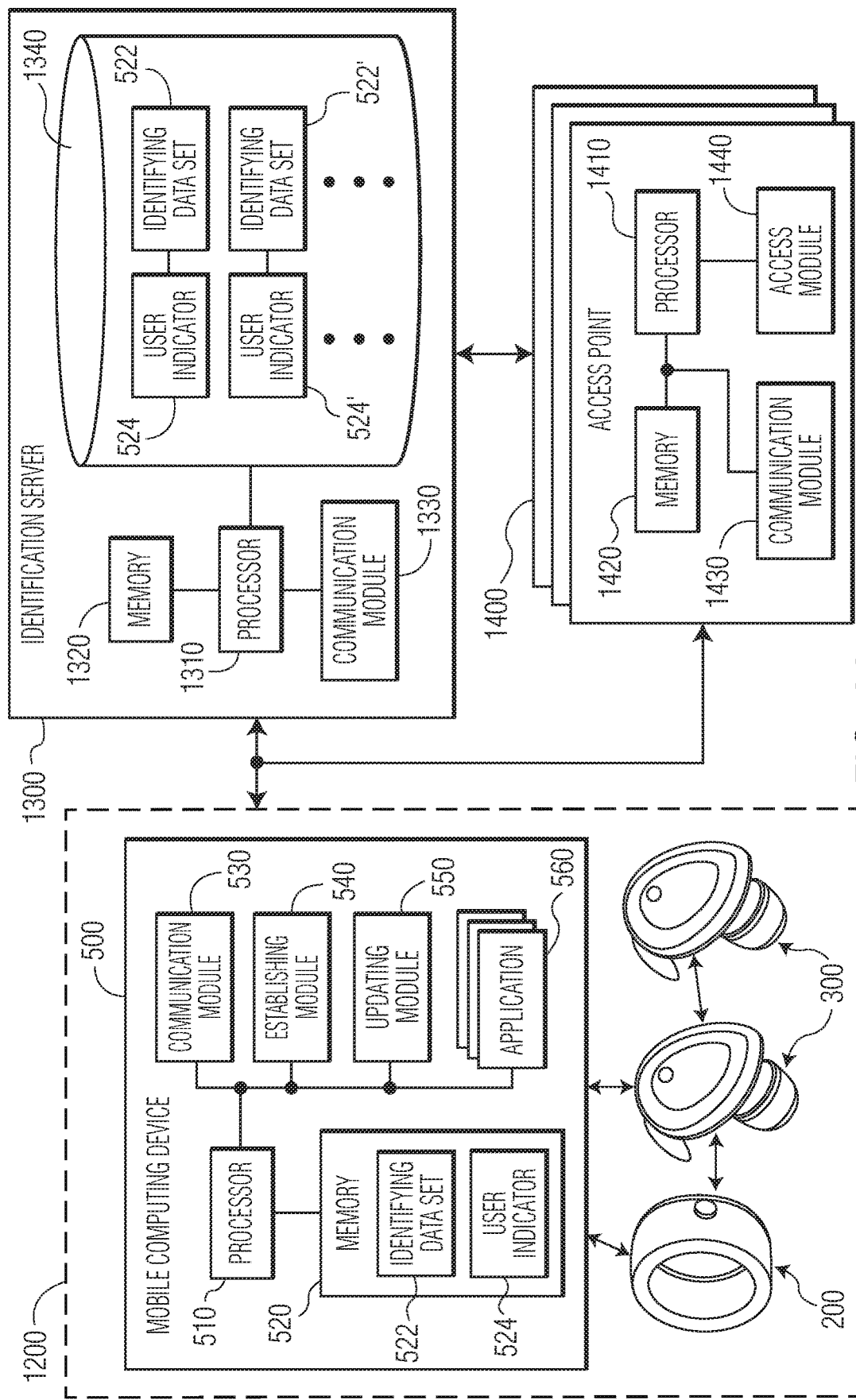
FIG. 26 is a schematic view of an identification system according to the invention.

An identification system according to an embodiment, as shown in FIG. 26, comprises the wearable electronic device 200, the earbuds 300, the mobile computing device 500, an identification server 1300 communicating with the mobile computing device 500, and a plurality of access points 1400 communicating with the mobile computing device 500 and the identification server 1300. The mobile computing device 500, the wearable electronic device 200 connected to the mobile computing device 500, and earbuds 300 connected to the wearable electronic device 200 and the mobile computing device 500 all correspond to a particular user 1200.

The mobile computing device 500, as shown in FIG. 26, includes a processor 510 and a memory 520 connected to the processor 510. The processor 510 may be any form of processor known to those with ordinary skill in the art. The memory 520 is a non-transitory computer readable medium storing software instructions executable by the processor 510.

The mobile computing device 500, as shown in FIG. 26, includes a communication module 530 connected to the processor 510. The communication module 530 is a device capable of wirelessly communicating data over short distances and long distances. In an embodiment, the communication module 530 includes a Bluetooth low energy device having a communication range of at least ten meters and a wi-fi antenna capable of communicating over the internet.

The mobile computing device 500, as shown in FIG. 26, includes an establishing module 540, an updating module 550, and a plurality of applications 560. Each of the modules 540, 550 and applications 560 are software stored on the memory 520 that are executable by the processor 510; the functions and features of the modules 540, 550 and applications 560 described in greater detail below are performed by execution of the processor 510. In an embodiment, the applications 560 can include a music playing application, a phone application, an Internet browser application, a social media application, a mapping application, and any other types of applications commonly used on mobile computing devices.

As shown in FIG. 26, an identifying data set 522 and a user indicator 524 are stored on the memory 520 of the mobile computing device 500. The user indicator 524 is entered by the user 1200 into the memory 520, for example using a known interface of the mobile computing device 500. In various embodiments, the user indicator 524 may be a user name, an account number, an email address, or any other piece of data used to indicate a particular account or user. The establishment and storing of the identifying data set 522 in the memory 520 in association with the user indicator 524 will now be described in greater detail.

Figure 27:
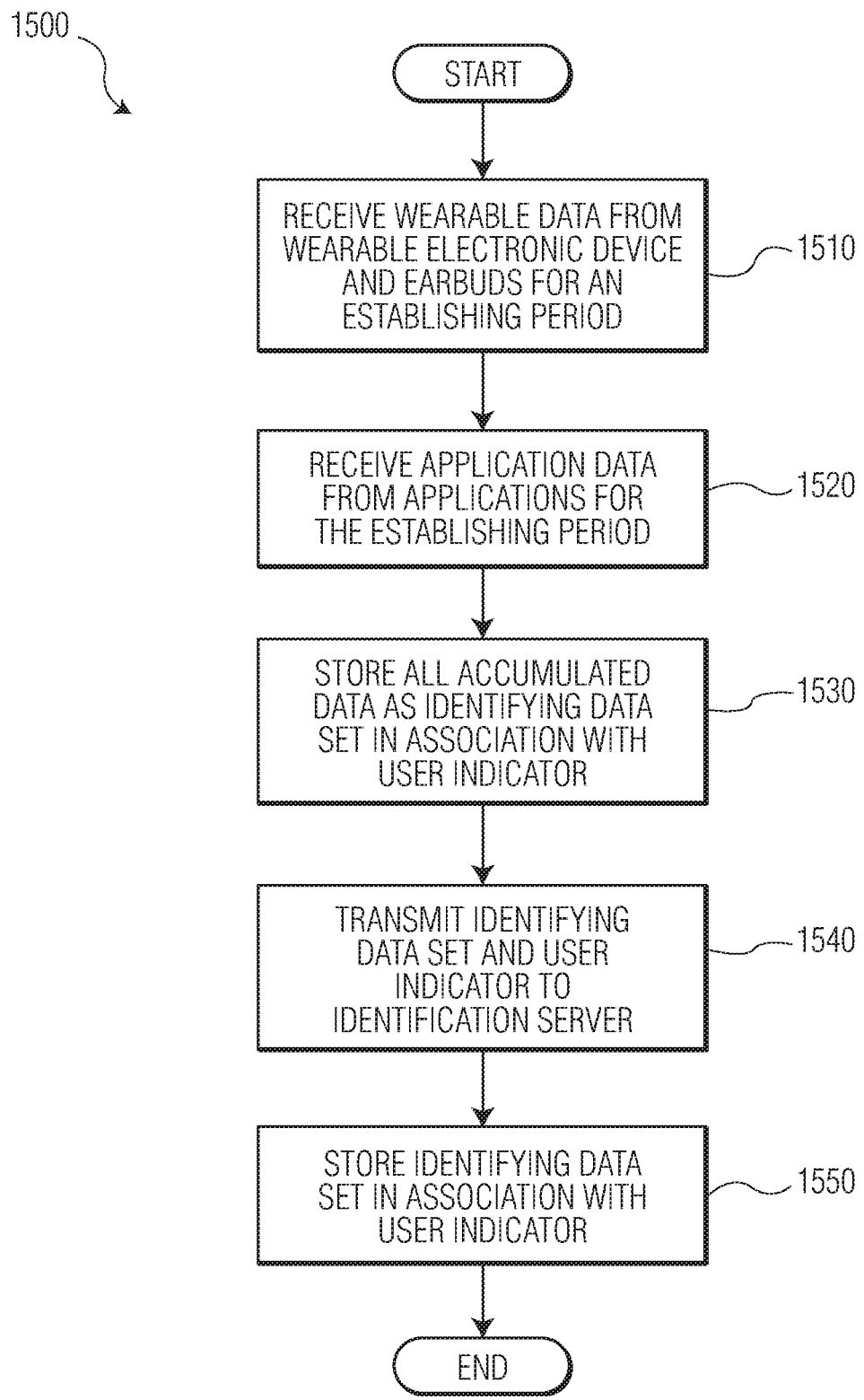
FIG. 27 is a flowchart of a process of establishing an identifying data set using the identification system.

A process 1500 of establishing the identifying data set 522 is shown in FIG. 27.

In a step 1510, shown in FIG. 27, the mobile computing device 500 communicates with the wearable electronic device 200 and the earbuds 300 through the communication module 530. The mobile computing device 500 receives a plurality of wearable data from the wearable electronic device 200 and the earbuds 300. The wearable data can include, for example, accelerometer 250 data, data from the plurality of capacitive plates 246, data from the battery management module 256, data from the sensors 380, data from the microphone 370, data from the speaker 360, and/or any other data that is capable of being gathered and transmitted by the wearable electronic device 200 and earbuds 300.

In a step 1520, as shown in FIG. 27, the mobile computing device 500 receives a plurality of application data from the applications 560 for the establishing period. The application data can include data on, for example, location, navigation, music, use of credit cards, web accounts held, devices connected to the mobile computing device 500, and any other data associated with how the particular user 1200 uses the mobile computing device 500 and applications 560.

In the steps 1510 and 1520, the mobile computing device 500 continues to receive the plurality of wearable data and the plurality of application data for an establishing period. The establishing period is determined to be sufficiently long to gather enough accumulated data, including both the wearable data and the application data, that the quantity and range of data is unique to the particular user 1200. For example, the accelerometer 250 data, data from the plurality of capacitive plates 246, data from the battery management module 256, data from the sensors 380, data from the microphone 370, data from the speaker 360, and location data, navigation data, and music data from the applications 560 gathered for the establishing period and considered as a whole is sufficiently different in measurement type, value, and frequency from other users that only the particular user 1200 corresponds to the accumulated data. In an embodiment, the establishing period is one week.

In a step 1530, as shown in FIG. 27, the processor 510 executes the establishing module 540 to store the gathered accumulated data as the identifying data set 522 in the memory 520. The identifying data set 522, after the establishing period, includes all of the wearable data and the application data gathered for the particular user 1200 in the establishing period. The identifying data set 522 is stored in association with the user indicator 524 in the memory 520 and is capable of uniquely identifying the user 1200 corresponding to the mobile computing device 500.

In a step 1540, as shown in FIG. 27, the processor 510 executes the establishing module 540 to transmit the identifying data set 522 and the user indicator 524 through the communication module 530 to the identification server 1300.

The identification server 1300, as shown in FIG. 26, includes a processor 1310 and a memory 1320 connected to the processor 1310. The processor 1310 may be any form of processor known to those with ordinary skill in the art. The memory 1320 is a non-transitory computer readable medium storing software instructions executable by the processor 1310. The identification server 1300 includes a communication module 1330 connected to the processor 1310. The communication module 1330 is a device capable of wirelessly communicating data over long distances. In an embodiment, the communication module 1330 includes a wi-fi antenna capable of communicating over the internet. The identification server 1300 includes an identification database 1340 connected to the processor 1310. In an embodiment, the identification server 1300 functions as cloud storage.

In a step 1550, as shown in FIG. 27, the identification server 1300 receives the identifying data set 522 and the user indicator 524 at the communication module 1330. The processor 1310 stores the received identifying data set 522 and user indicator 524 in the identification database 1340. The identification server 1300 is used with a plurality of different users 1200; as shown in FIG. 26, the plurality of different identifying data sets 522, 522' are stored in the identification database 1340 in association with the corresponding user indicator 524, 524' of a plurality of different users 1200.

Figure 28:
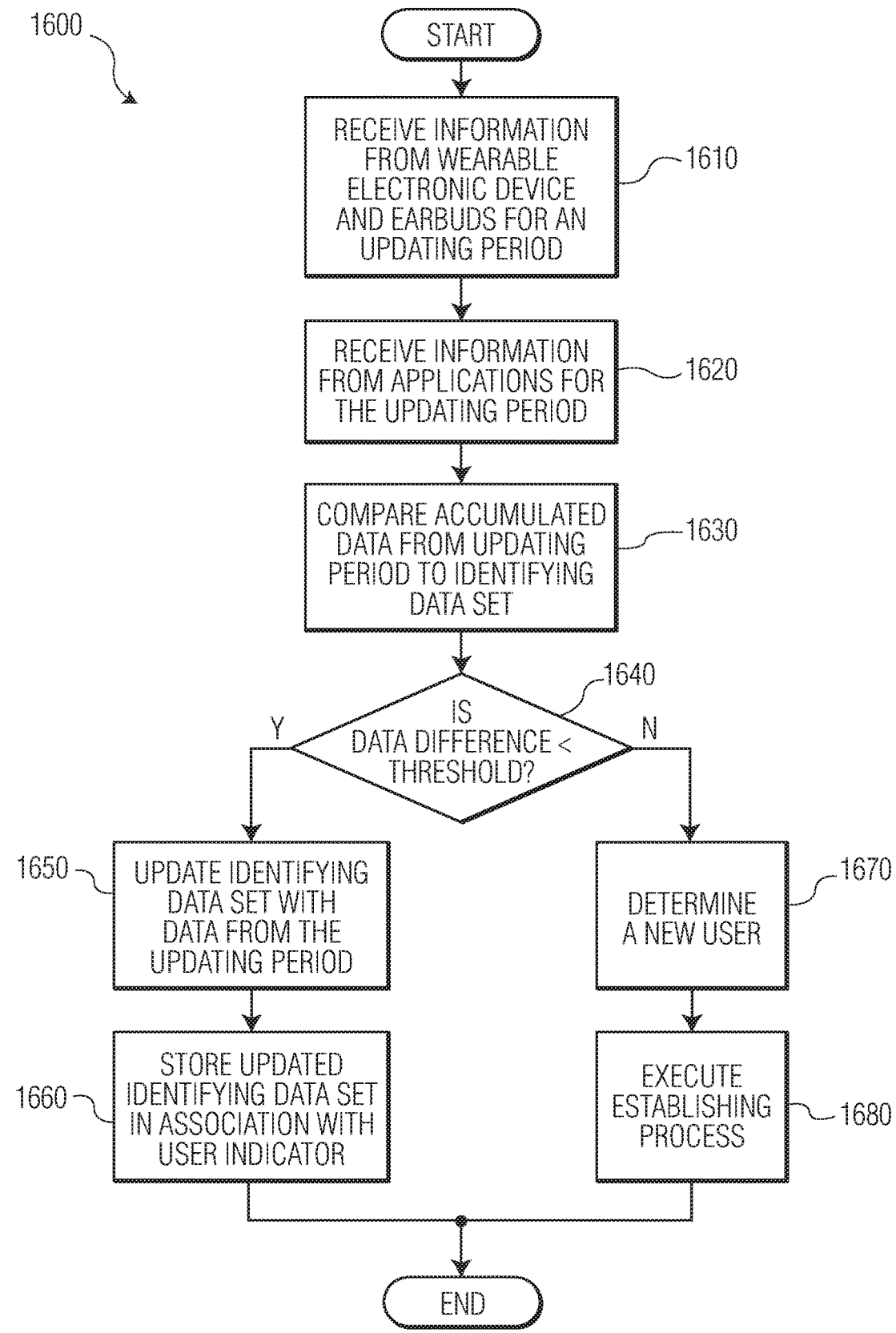
FIG. 28 is a flowchart of a process of updating the identifying data set using the identification system.

A process 1600 of updating the identifying data set 522 of the user 1200 is shown in FIG. 28 and will now be described in greater detail. The process 1600 loops continuously as long as an identifying data set 522 is stored in the memory 520.

In a step 1610 shown in FIG. 28, with the identifying data set 522 stored in the memory 520, the mobile computing device 500 continues to receive the wearable data from the wearable electronic device 200 and the earbuds 300 for an updating period. In a step 1620, the mobile computing device 500 continues to receive the application data from the applications 560 for the updating period. The updating period is shorter than the establishing period. The updating period is long enough to include changes in the accumulated data that includes the wearable data and the application data. In various embodiments, the updating period may be less than an hour, may be one hour, or may be a number of hours.

In a step 1630, the processor 510 executes the updating module 550 to compare the accumulated data from the updating period to the data in the identifying data set 522 stored in the memory 520.

As shown in a step 1640 in FIG. 28, a threshold that is part of the updating module 550 is compared to a difference between the accumulated data from the updating period and the data in the identifying data set 522. The updating module 550 executed by the processor 510 considers each of the various elements of data in the identifying data set 522 and in the accumulated data from the updating period, including a change in type, value, and frequency of the elements of data. The algorithm of the updating module 550, when executed by the processor 510, determines whether the accumulated data in the updating period, as a whole, is more different or less different than a threshold in comparison with the identifying data set 522. For example, if the data from the sensors 380 in the wearable data indicates that the user's heart rate is sustained at a different level than in the identifying data set 522, the application data indicates that the user is in a new country, and the mobile computing device 500 is connected with multiple different devices, the updating module 550 may determine that the changes exceed the threshold. Conversely, for example, if the data from the sensors 380 in the wearable data indicates that the user's heart rate was only temporarily different than in the identifying data set 522, the user's location is new but nearby previous locations, and the mobile computing device 500 is connected with one new device, the updating module 550 may determine that the changes are below the threshold.

As shown in a step 1650 in FIG. 28, if the differences between the accumulated data from the updating period and the identifying data set 522 are less than the threshold, the processor 510 executes the updating module 552 to update the identifying data set 522 with the accumulated data from the updating period. The identifying data set 522 would then include the accumulated data from the establishing period and the accumulated data from the updating period.

In a step 1660 shown in FIG. 28, the mobile computing device 500 transmits the updated identifying data set 522 and the user indicator 524 through the communication module 530 to the identification server 1300. The identification server 1300 receives the updated identifying data set 522 and the user indicator 524 and stores the updated identifying data set 522 in association with the user indicator 524 in the identification database 1340.

If the differences between the accumulated data from the updating period and the identifying data set 522 are greater than the threshold, as shown in a step 1670 in FIG. 28, the updating module 550 determines that a new user 1200 is using the mobile computing device 500, the wearable computing device 200, and the earbuds 300. The updating module 550 prompts the user for a new user indicator 524 and, as shown in a step 1680, the process 1500 shown in FIG. 27 is executed for the new user.

Figure 29:
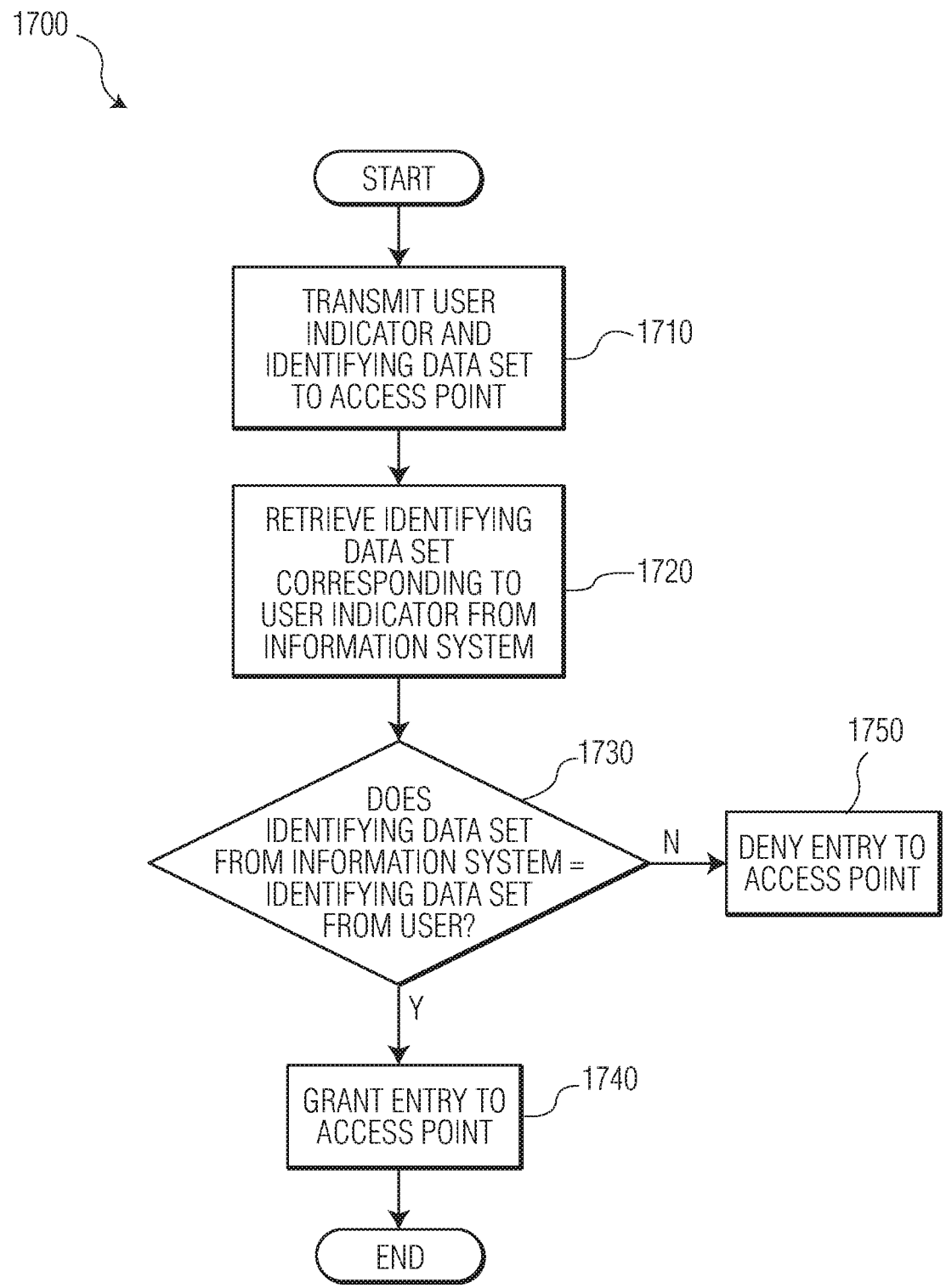
FIG. 29 is a flowchart of a process of accessing an access point of the identification system.

A process 1700 of accessing one of the plurality of the access points 1400 is shown in FIG. 29 and will now be described in greater detail.

Each of the access points 1400, shown in FIG. 26, may be any type of node on the Internet of Things (IoT) that requires a validation or password to access. In various embodiments, the access point 1400 may be a physical access point such as a lock for a building or a car, a digital access point such as an online account accessed through a computer terminal, or any other type of IoT node that could require a validation or password.

The access point 1400, as shown in FIG. 26, includes a processor 1410 and a memory 1420 connected to the processor 1410. The processor 1410 may be any form of processor known to those with ordinary skill in the art. The memory 1420 is a non-transitory computer readable medium storing software instructions executable by the processor 1410. The access point 1400 includes an access module 1440. The access module 1440 is software stored on the memory 1420 that is executable by the processor 1410; the functions and features of the access module 1440 described in greater detail with reference to the process 1700 shown in FIG. 29 are performed by execution of the processor 1410.

The access point 1400, as shown in FIG. 26, includes a communication module 1430 connected to the processor 1410. The communication module 1430 is a device capable of wirelessly communicating data over long distances. In an embodiment, the communication module 1430 includes a wi-fi antenna capable of communicating over the internet.

The process 1700 begins when the user 1200 attempts to access the access point 1400. As shown in FIG. 29, in a step 1710, the mobile computing device 500 transmits the user indicator 524 and the identifying data set 522 to the access point 1400 through the communication module 530. The access point 1400 receives the user indicator 524 and the identifying data set 522 at the communication module 1430.

In a step 1720 shown in FIG. 29, the processor 1410 executes the access module 1440 to communicate with the identification server 1300 through the communication module 1430. The access module 1440 requests the identifying data set 522 from the identification database 1340 that corresponds to the user indicator 524 received from the user 1200 in the step 1710. The processor 1310 of the identification server 1300 retrieves the identifying data set 522 from the identification database 1340 corresponding to the received user indicator 524 and transmits the identifying data set 522 to the access point 1400.

In a step 1730 shown in FIG. 29, the access module 1440 compares the identifying data set 522 received from the identification server 1300 to the identifying data set 522 received from the user 1200 in the step 1710. If the identifying data sets 522 match, as shown in a step 1740, the access module 1440 determines that the user 1200 is validated and grants entry to the access point 1400. In various embodiments, for example, granting entry to the access point 1400 may include unlocking a physical lock or granting access to a secure section of a website. If the identifying data sets 522 do not match, as shown in a step 1750, the access module determines that the user 1200 is not validated and denies entry to the access point 1400. In the information system, the established identifying data set 522 associated with the user indicator 524 can thereby function as an automatically generated and updated password for a variety of access points 1400.

What is claimed is:

1. An identification system, comprising:
   a mobile computing device having a memory and an establishing module establishing an identifying data set stored in the memory, the identifying data set includes an accumulated data gathered at the mobile computing device over an establishing period and is capable of uniquely identifying a user corresponding to the mobile computing device, the mobile computing device includes a plurality of applications and the identifying data set includes a plurality of application data from the plurality of applications;
   a wearable electronic device communicating with the mobile computing device, the identifying data set includes a plurality of wearable data from the wearable electronic device; and
   an earbud wirelessly connected with the wearable electronic device and the mobile computing device, the plurality of wearable data includes data from the earbud.

2. The identification system of claim 1, wherein the wearable electronic device includes:
   a ring body defining an annular receiving space within the ring body and having an interface disposed on an exterior of the ring body; and
   a substrate disposed in the annular receiving space and having a plurality of capacitive plates positioned proximate the interface.

3. The identification system of claim 2, wherein the wearable electronic device includes an accelerometer disposed on the substrate.

4. The identification system of claim 1, wherein the earbud has a heartrate sensor and a body temperature sensor.

5. The identification system of claim 1, further comprising an identification server communicating with the mobile computing device, the identification server having an identification database storing the identifying data set in association with a user indicator corresponding to the user.

6. The identification system of claim 5, further comprising an access point communicating with the mobile computing device and the identification server.

7. The identification system of claim 6, wherein the access point has an access module determining whether to grant the user entry to the access point based on the identifying data set.

8. The identification system of claim 1, wherein the mobile computing device has an updating module updating the identifying data set based on the accumulated data gathered at the mobile computing device over an updating period after the establishing period.

9. The identification system of claim 8, wherein the updating period is shorter than the establishing period.

10. The identification system of claim 8, wherein the updating module determines whether a new user is using the mobile computing device.

11. A process of establishing and updating an identifying data set of a user, comprising:
provide a mobile computing device having a memory;
receiving an accumulated data at the mobile computing device over an establishing period;
storing the accumulated data gathered over the establishing period as the identifying data set in a memory of the mobile computing device, the identifying data set is capable of uniquely identifying the user corresponding to the mobile computing device;
receiving the accumulated data at the mobile computing device over an updating period after the establishing period;
comparing a difference between the identifying data set and the accumulated data from the updating period to a threshold;
updating the identifying data set with the accumulated data from the updating period if the difference is less than the threshold; and
determining a new user if the difference is greater than the threshold.

12. The process of claim 11, further comprising providing a wearable electronic device communicating with the mobile computing device, the identifying data set includes a plurality of wearable data from the wearable electronic device.

13. The process of claim 12, wherein the mobile computing device includes a plurality of applications and the identifying data set includes a plurality of application data from the plurality of applications.

14. The process of claim 11, further comprising:
transmitting the identifying data set and a user indicator corresponding to the user to an identification server; and
storing the identifying data set in association with the user indicator on an identification database of the identification server.

15. A process of accessing an access point using an identifying data set of a user, comprising:
providing a mobile computing device having a memory with an identifying data set stored in the memory, the identifying data set includes an accumulated data gathered at the mobile computing device over an establishing period and is capable of uniquely identifying a user corresponding to the mobile computing device;
granting the user entry to the access point based on the identifying data set;
receiving the identifying data set and a user indicator corresponding to the user from the mobile computing device at the access point; and
retrieving the identifying data set corresponding to the user indicator from an identification server, the granting step is based on an evaluation of an equivalence of the identifying data set received from the identification server and the identifying data set received from the mobile computing device.

* * * * *